United States Patent
Zafirelis et al.

(10) Patent No.: US 6,808,508 B1
(45) Date of Patent: Oct. 26, 2004

(54) METHOD AND SYSTEM FOR CLOSED CHEST BLOOD FLOW SUPPORT

(75) Inventors: Zafiris G. Zafirelis, Needham, MA (US); John C. Marous, III, Pittsburgh, PA (US); Yih-Choung Yu, Pittsburgh, PA (US); Kirk A. Lehmann, Library, PA (US); Gregory A. Johnson, Pittsburgh, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 96 days.

(21) Appl. No.: 09/661,413

(22) Filed: Sep. 13, 2000

(51) Int. Cl.$^7$ ............................................ A61M 37/00
(52) U.S. Cl. ....................... 604/131; 604/6.11; 604/151
(58) Field of Search ............................. 604/6.11, 8–10, 604/27, 30, 35, 39, 40, 43, 48, 131, 151, 500, 4, 4.01, 6.06, 6.16, 96.01, 532; 600/16

(56) References Cited

U.S. PATENT DOCUMENTS

| | | | | |
|---|---|---|---|---|
| 4,994,027 A | * | 2/1991 | Farrell ........................ | 604/510 |
| 5,190,528 A | * | 3/1993 | Fonger et al. ............... | 604/171 |
| 5,314,418 A | * | 5/1994 | Takano et al. ............... | 604/540 |
| 5,449,342 A | * | 9/1995 | Hirose et al. ............... | 604/6.11 |
| 5,840,070 A | * | 11/1998 | Wampler ..................... | 604/131 |
| 5,885,238 A | * | 3/1999 | Stevens et al. .............. | 604/6.14 |
| 5,916,193 A | | 6/1999 | Stevens et al. | |
| 5,957,879 A | * | 9/1999 | Roberts et al. ............ | 604/6.06 |
| 6,083,260 A | * | 7/2000 | Aboul-Hosn ................ | 623/3.14 |
| 6,110,139 A | * | 8/2000 | Loubser ....................... | 604/30 |
| 6,217,546 B1 | * | 4/2001 | Hinchliffe et al. ........ | 604/96.01 |

* cited by examiner

Primary Examiner—Gregory L. Huson
Assistant Examiner—Huyen Le
(74) Attorney, Agent, or Firm—Ansel M. Schwartz

(57) ABSTRACT

A system for assisting flow of blood by a patient's heart. The system includes a transseptal cannula adapted to be inserted percutaneously in the femoral vein and extend through the atrial septum from the right atrium to the left atrium. The system includes a blood pump mechanism having a blood pump for pumping blood received from the transseptal cannula that has been oxygenated at specified flow rates over a range of physiological pressures. The blood pump is connected to the transseptal cannula. The system includes a perfusion cannula adapted to be inserted percutaneously in the femoral artery for returning oxygenated blood to the atrial system of the patient. The perfusion cannula is connected to the blood pump. A method for assisting blood flow by a patient's heart. The method includes the steps of inserting percutaneously in the femoral vein of the patient and extending through the atrial septum from the right atrium to the left atrium a transseptal cannula. Next there is the step of inserting percutaneously in the femoral artery a perfusion cannula for returning oxygenated blood to the arterial system of the patient. Then there is the step of pumping blood with a blood pump connected to the transseptal cannula and the perfusion cannula at specified flow rates over a range of physiological pressures.

45 Claims, 28 Drawing Sheets

SYSTEM 300

PATIENT PORTION
350

← ELAPSED_ms →

PULSE RATE = NUMBER OF TRAILING EDGES COUNTED DURING THE TIME INTERVAL.
ELAPSED_ms = ACTUAL NUMBER OF MILLISECONDS IN THE TIME INTERVAL.

14/21 FR. PVTC TWO STAGE DILATOIR

DILATOR TIP

13 FR. PVTC CATHETER

CANNULA FITTING

HUB

21 FR. PVTC CANNULA

MARKER BAND

CLAMP AREA

3/8" BARBED CONNECTOR

METHOD AND SYSTEM FOR CLOSED CHEST BLOOD FLOW SUPPORT

FIELD OF THE INVENTION

The present invention is related to a cardiac assist system having a transseptal cannula that extends through the atrial septum from the right atrium to the left atrium of the patient and a perfusion cannula that extends into the arterial system of the patient for circulating oxygenated blood throughout the patient. More specifically, the present invention is related to an extracorporeal blood pump, connected to the transseptal cannula at the pump inlet and the perfusion cannula at the pump outlet, that pumps blood at specified flow rates over a range of physiological pressure and is held in place on the patient's leg.

BACKGROUND OF THE INVENTION

For short term (hours to days) use in supporting significant circulation (1–3.5 LPM) of oxygenated blood, there is a need for simple equipment in a hospital that can be quickly connected to the patient without surgical intervention and that can provide bypass blood flow to the patient. The present invention provides a quick and relatively simple way of operation to assist the heart without an open-chest surgery.

SUMMARY OF THE INVENTION

The present invention pertains to a system supporting circulation of oxygenated blood. The system comprises a transseptal cannula set adapted to be inserted percutaneously in the femoral vein and extend through the atrial septum from right atrium to left atrium, a blood pump mechanism, connected to the transseptal cannula through the pump inlet and controlled by an external microprocessor based blood pump controller, for pumping blood received from the patient's heart, a perfusion cannula adapted to be inserted percutaneously in the femoral artery and connected to the pump outlet for returning oxygenated blood to the arterial system of the patient. The cannula set consists of a cannula, a catheter, and a dilator. The catheter and dilator are used for insertion of the cannula.

The present invention pertains to a method and a process for assisting a patient's heart. The method comprises a step of inserting a transseptal cannula percutaneously in the femoral vein of the patient and extending through the atrial septum from the right atrium to the left atrium. Next there is a step of inserting a perfusion cannula percutaneously in the femoral artery for returning oxygenated blood to the arterial system of the patient. Next is preferably a step of connecting the two cannulae to the pump. Then there is a step of pumping blood with a blood pump connected to the transseptal cannula and the perfusion cannula at specified flow rates over a range of physiological pressures. This step preferably includes control of the pump and monitoring of the control system and pump by an external pump controller in such a manner as to detect, manage, and alert the user to the applicable potential system faults without dedicated human monitoring.

In addition, the system of the present invention can be used to quickly access or redistribute a patient's blood to a certain destination in a patient's body by changing appropriate sizes of cannulae connected to the pump inlet and outlet.

BRIEF DESCRIPTION OF THE DRAWINGS

In the accompanying drawings, the preferred embodiment of the invention and preferred methods of practicing the invention are illustrated in which.

DETAILED DESCRIPTION

Figure 11:
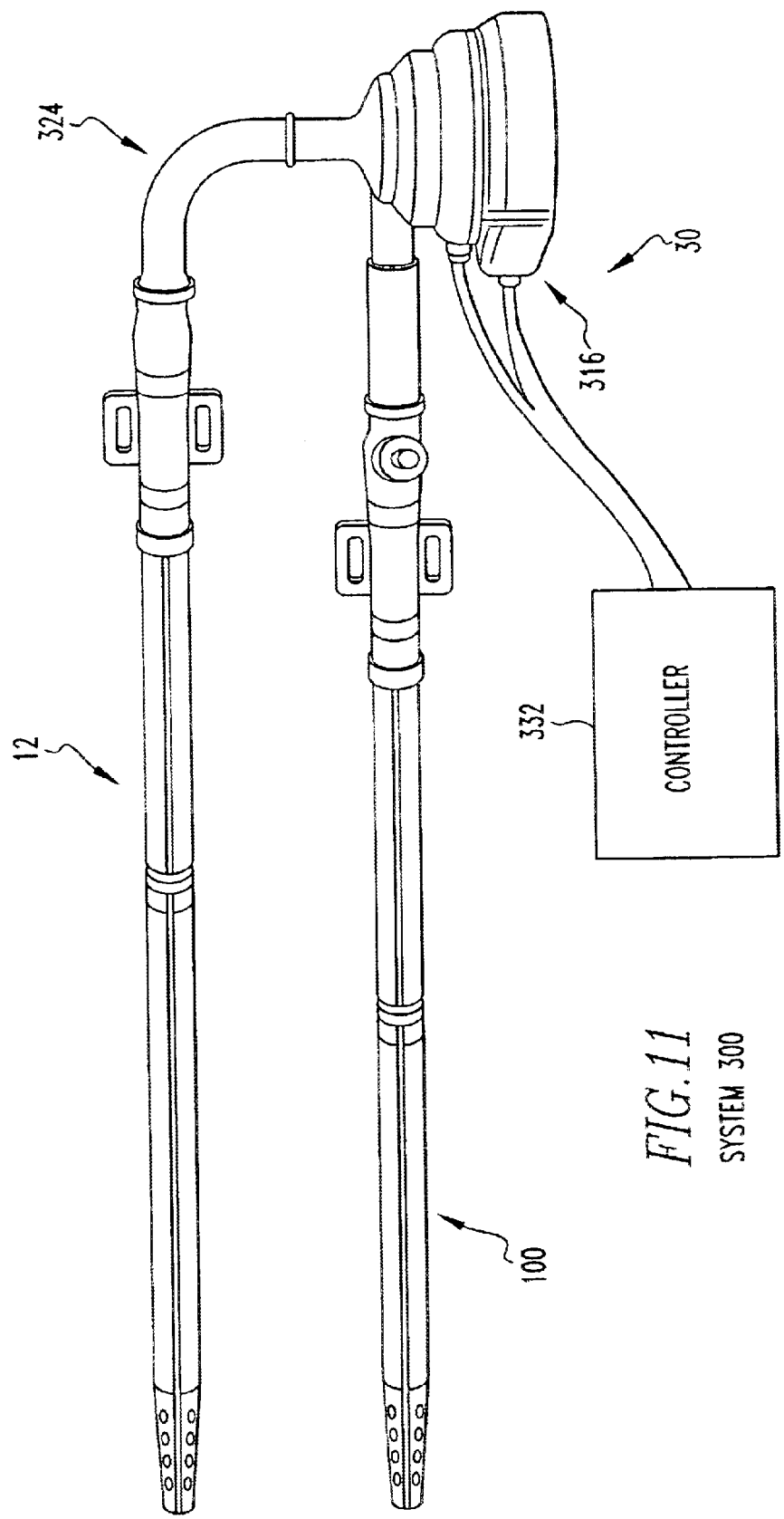
FIG. 11 is a schematic representation of the fluid pathway components of the present invention.

Referring now to the drawings wherein like reference numerals refer to similar or identical parts throughout the several views, and more specifically to FIG. 11 thereof, there is shown a system 300 for assisting flow of blood by a patient's heart. The system 300 comprises a transseptal cannula 12 adapted to be inserted percutaneously in the femoral vein and extend through the atrial septum from the right atrium to the left atrium. The system 300 comprises a perfusion cannula 100 adapted to be inserted percutaneously in the femoral artery. The system 300 comprises a blood pump mechanism 30 having a blood pump 316 (driven by a brushless DC motor), connected to the transseptal cannula 12 at the pump inlet, for pumping oxygenated blood received from the left atrium through the transseptal cannula 12 and returning the blood to the arterial system of the patient through the perfusion cannula 100 connected to the blood pump 316 at the pump outlet. The blood pump 316 is controlled by a controller 332 that monitors key system operating parameters to detect and manage faults and to alert operators.

Fault tolerance of the system is offered by providing redundant mechanisms for pump operation and for monitoring functions. Pump operation must propel blood at sufficient flow rates (1–3.5 LPM) without destroying red blood cells, without causing clotting of the blood, without causing immune system or other biocompatibility compromise or reaction, and must locate and center themselves without offering a wear surface that can cause blood damage or clotting over time or can cause variable power loss over time, as power loss is used as a performance monitor. Reliable operation must be maintained even through a wide variety of system, component, or human faults.

The AB-180 XC System, as it is referred to, offers atraumatic contact with red blood cells by virtue of the smooth surface finishes of the blood contacting surfaces, the gradual radiuses of the impeller, and does not allow locations for stagnant blood to accumulate and form clots. In addition to these smooth geometries, it is designed to be placed within 3 feet of the blood egress from the body, as the small amount of artificial material minimizes complications. To provide further resistance to thrombus formation, an anti-coagulant is infused directly into the blood chamber of the pump, where concentration of anti-coagulant is high enough to deter clotting. But since the pump volume is small, the amount of infused anti-coagulant is small enough to achieve minimal effect on systemic concentration of anti-coagulant when the blood flowing out of the pump is disbursed throughout the body. This is important, as the anti-coagulant concentration throughout the body is then small enough to prevent additional risk of internal bleeding elsewhere in the patient. Clots can also form when blood flow drops to low rates (<0.5 LPM), which can happen if the transseptal cannula becomes clogged or kinked, if the patient bleeds internally, or if a cannula becomes dislodged. Any of these events cause an alarm condition from the reduced blood flow.

Pump wear is a major issue with blood pumps, as any wear can cause blood damage and/or clotting. The infusion system used to infuse anti-coagulant into the blood chamber also performs a useful bearing function. While the main bearing function, or centering and locating of the rotating part of the pump, is performed by the interaction of the stator and rotor electromagnetic interactions, the rotating impeller is also centered by a) the impeller/seal sliding contact and b) the fluid film and fluid lift pads in the motor chamber. Whenever the rotor becomes out of center, the fluid film prevents rotor and stator contact, thus providing fault tolerance of the electromagnetics. In the motor chamber, the fluid film is propelled radially as the rotor rotates. As lift pads are encountered in the lower chamber surface, fluid is propelled axially into the surface of the rotor, thus 'lifting' it away from the stator surface, where contact would cause wear. This fluid is pumped by a constant flow pump, which provides a stable flow of infusate into the lower chamber. This constant flow builds pressure in the lower chamber, and as this pressure exceeds the pressure across the seal in the upper, or blood flow chamber, the infusate is pressed through the seal and into the blood chamber, where the anti-coagulation prevents clotting. The infusate fluid thus provides a third bearing mechanism and a cooling mechanism for the seal/rotor contact area. Loss of infusate flow can then be used as an indicator of a fault in the bearing system, which can then allow a user alarm to correct the infusate system or the pump bearing system prior to any patient injury. The mechanism of the determination of infusate flow is described elsewhere.

Another mechanism for system fault is the presence of air in the system, which can happen in some circuits when the pressure is reduced to dangerous levels. This can occur in larger pumps or in longer and smaller cannula, which involve more pressure drop. The pump design, by its small size, prevents any such cavitation by means of low pressure. The mechanism of connections between the components prevents any injection of air into these joints, which can occur with the negative pressure associated with high pressure drop and long, small diameter cannulae. Without this mechanism of connection, and by connecting arbitrary components, dangerous pressures can result and can cause cavitation and/or air injection at the connection joints.

Figure 26A:
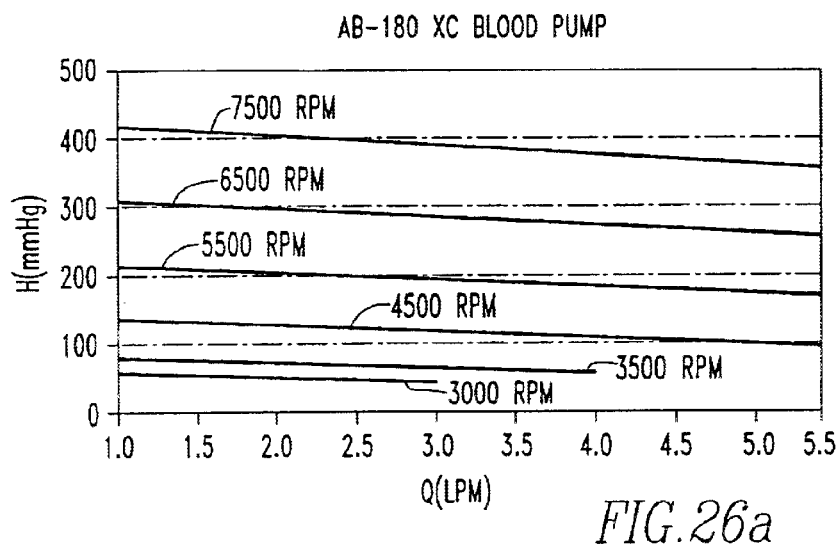
FIG. 26a is a graph of pressure versus flow of the blood pump.
Figure 26B:
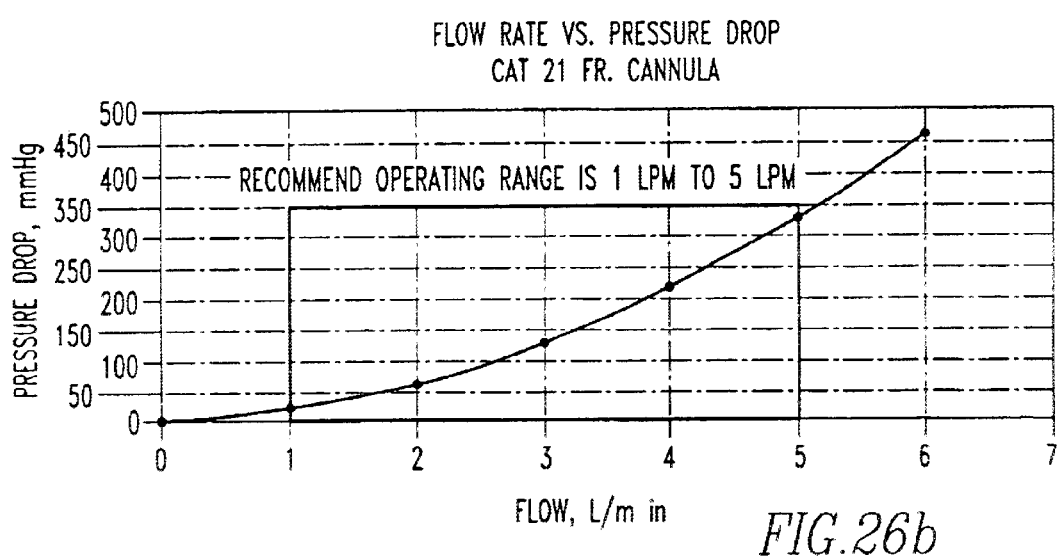
FIG. 26b is a graph of flow rate versus pressure drop.
Figure 26C:
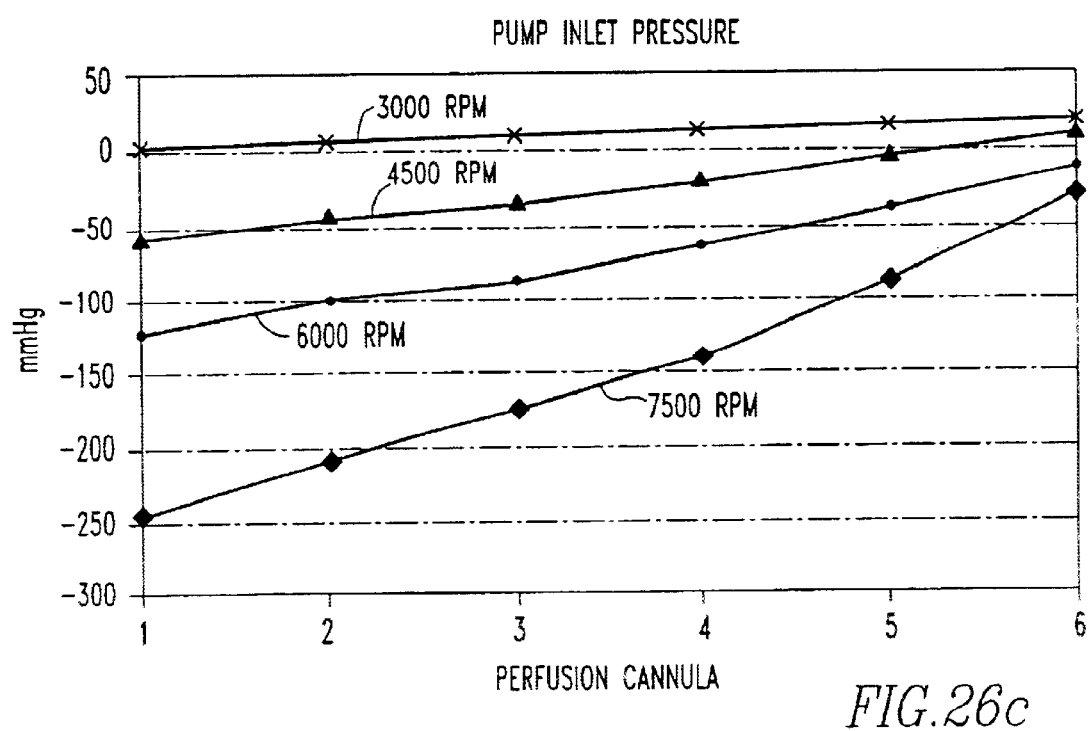
FIG. 26c is a graph regarding pump inlet pressure.

The flow characteristics of the Pump over a range of conditions, performed with perfusate at the viscosity of 3.5 cP (35% Glycerol+65% Saline @ 23° C.) is shown in FIG. 26a. The flow rates represent the relationship between RPM and the pressure differential between the inflow port and the outflow port. An estimated flow rate can be determined by using this chart, the RPM of the Pump and the pressure differential of the inlet to outlet ports. The pressure drop characteristics of the transseptal cannula are shown in FIG. 26b, with the box indicating the limits as specified with the AB-180 pump. The key issue is that the low pressure rise of the pump, in combination with the pressure drop of the cannula, does not allow any point in the circuit to obtain pressures lower than −350 mmHg, which is the point at which gases can be removed from the blood solution. Including the flow characteristics of the pump, the transseptal cannula, and the possible sizes of perfusion cannulae, the vacuum pressure created at the pump inlet can be solved at different pump speeds as shown in FIG. 26c. Since the pump inlet pressure is always higher than −350 mmHg, cavitation will not happen in the system over the recommended flow range against physiologic pressure.

All electrical control functions are redundant to provide enhanced reliability. And alarms are used to notify operators of potentially unsafe conditions rather than to stop the pump until replacement of control is maintained. All power systems are duplicated, and all control systems are watchdogged to warn of failures of standby monitor functions. Without these failsafe operations, tolerance of system, component, or human faults could not be offered.

Figure 17:
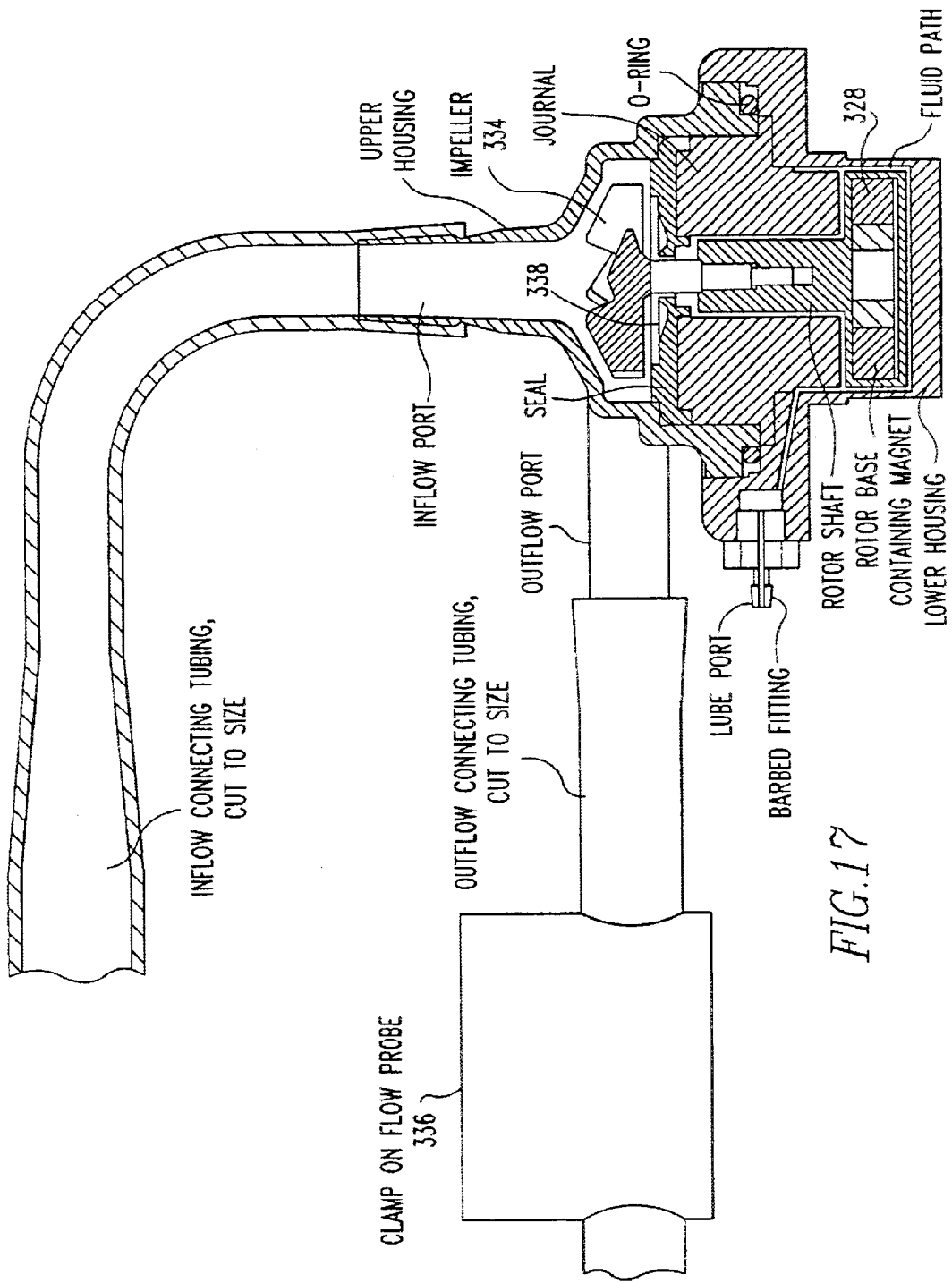
FIG. 17 is a schematic representation of a cross sectional view of the pump with a flow probe.
Figures 18, 19:
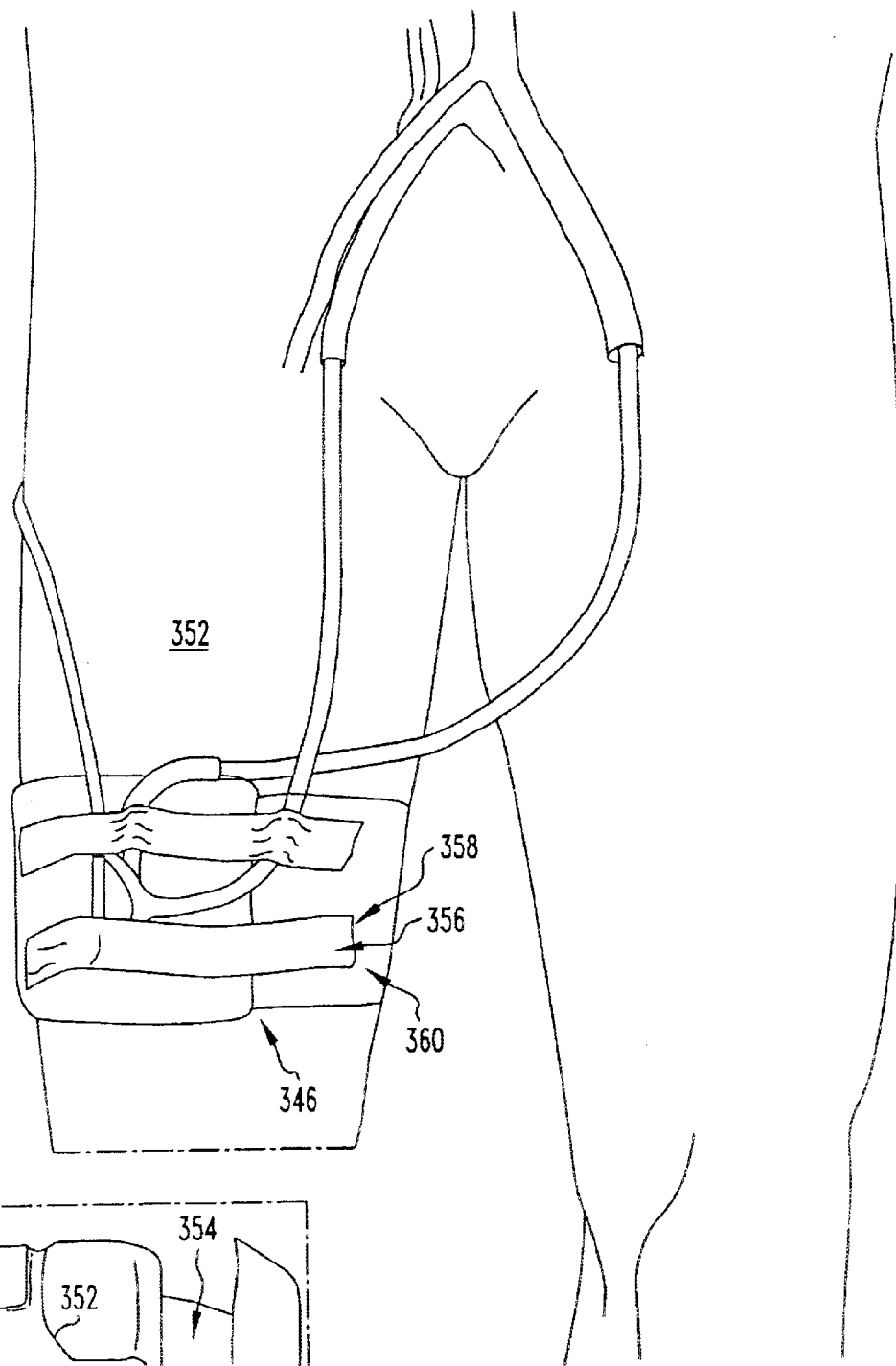
FIG. 18 is a schematic representation of the holding mechanism with the pump on the leg of a patient.
FIG. 19 is a schematic representation of the holding mechanism.
Figure 20:
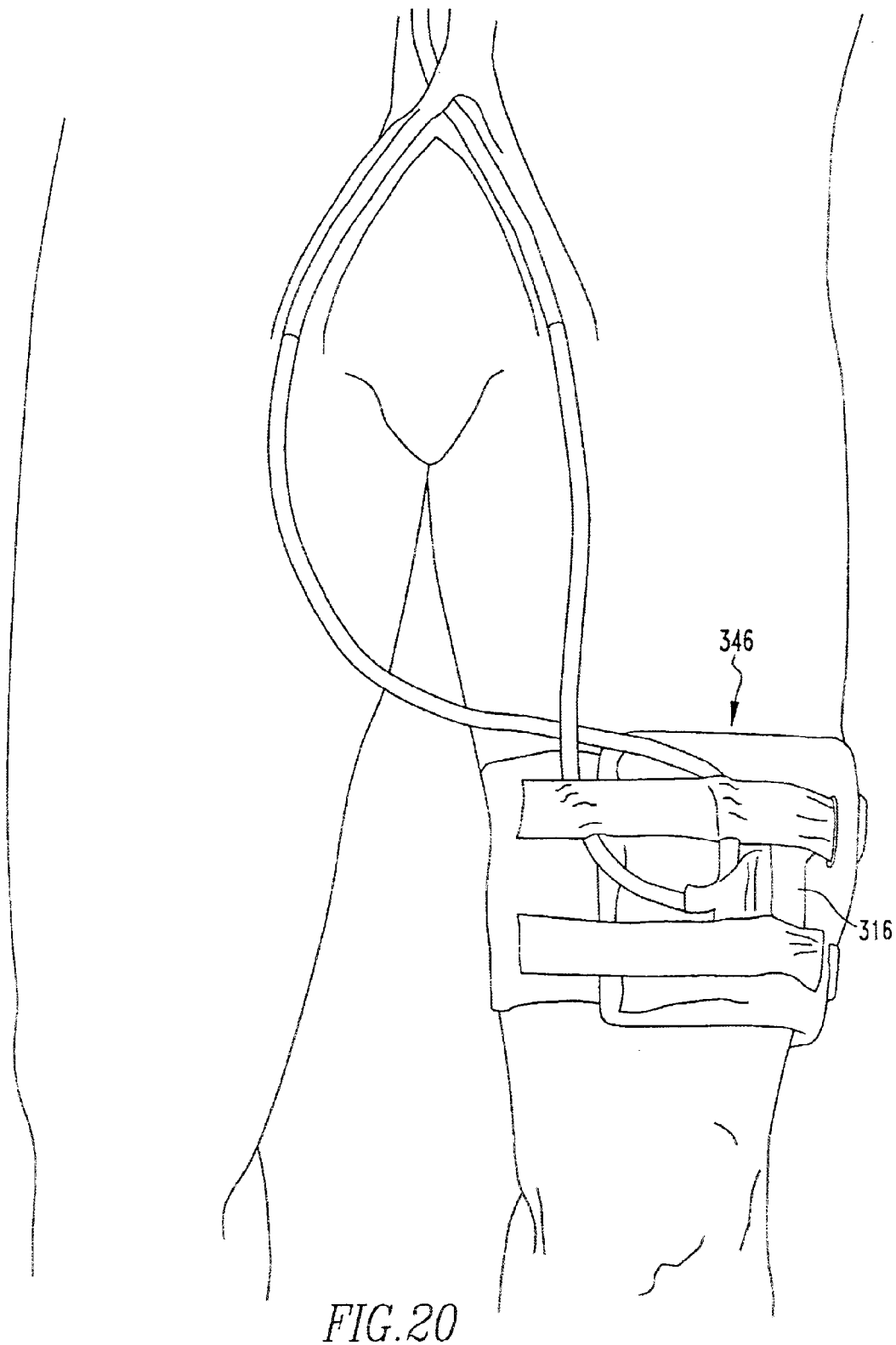
FIG. 20 is a schematic representation of the holding mechanism with the pump on the leg of the patient.
Figure 22:
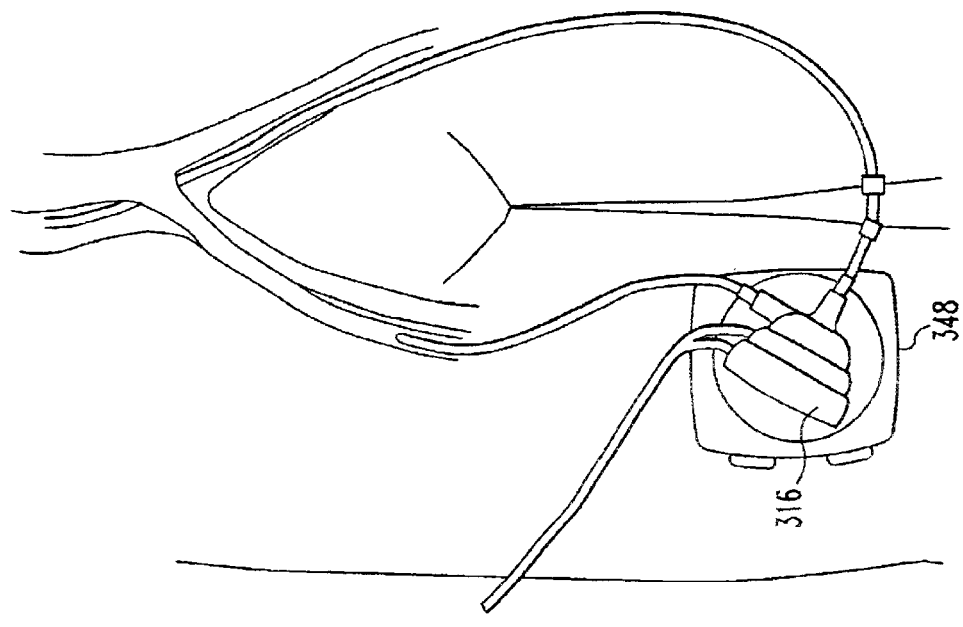
FIG. 22 is a schematic representation of the pump at an angle of 20 degrees from normal on the leg of a patient.
Figure 21:
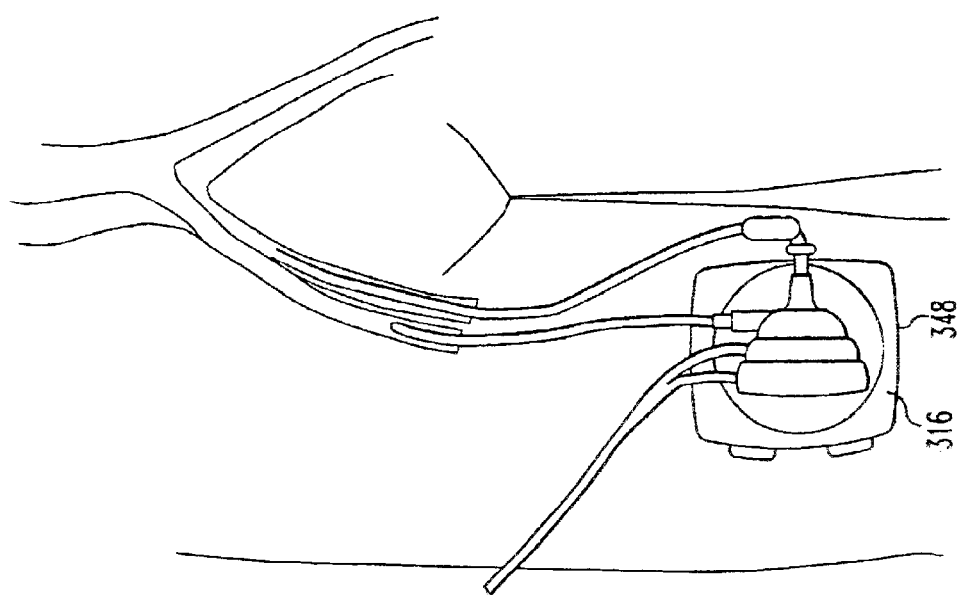
FIG. 21 is a schematic representation of the pump in a normal position on the leg of a patient.
Figure 23:
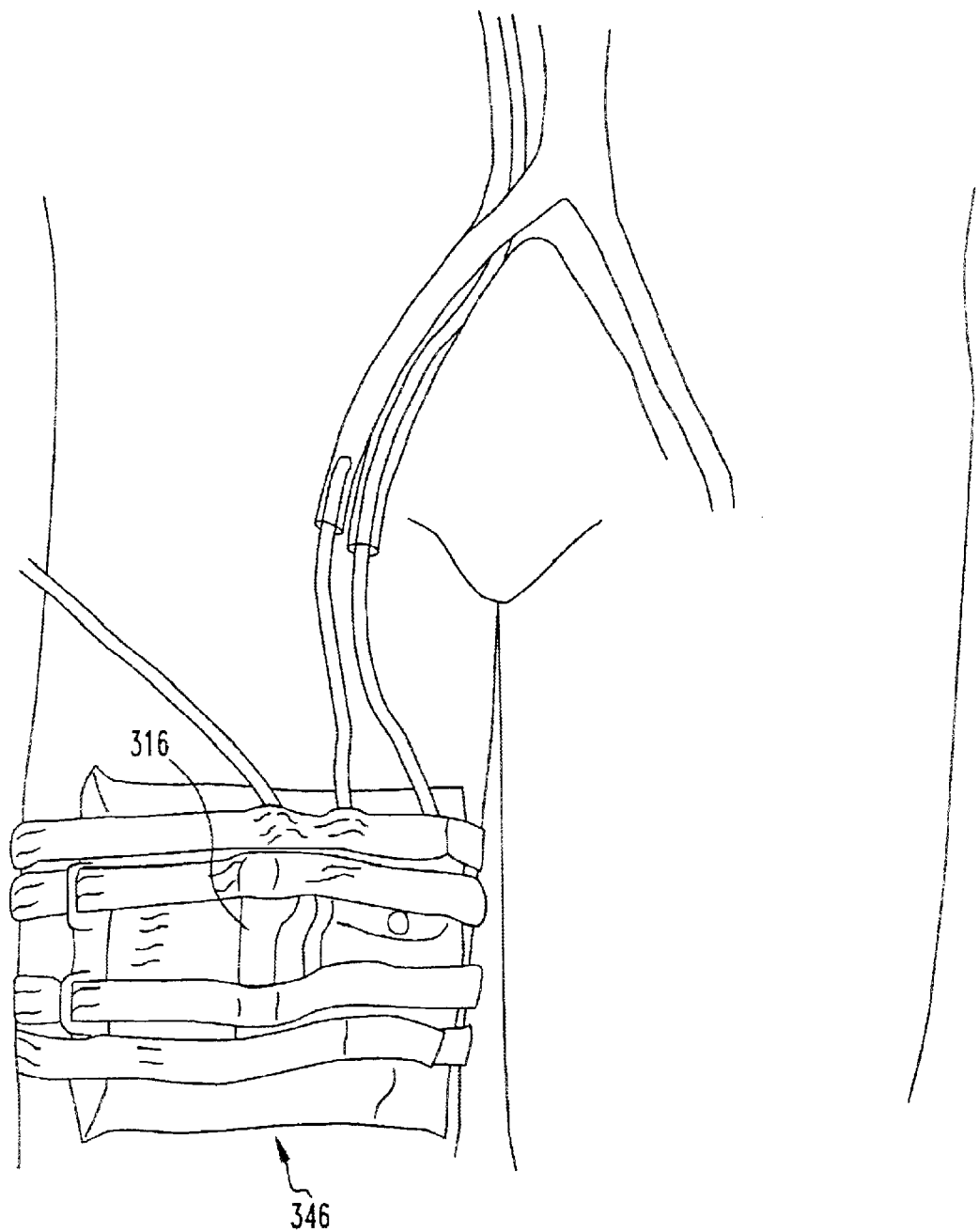
FIG. 23 is a schematic representation of the holding mechanism with the pump on the leg of the patient.

Preferably, the blood pump mechanism 30 includes a transseptal clamp mechanism 322 which clamps the blood pump 316 to the transseptal cannula 12 to avoid undesired disconnection of the blood pump 316 and the transseptal cannula 12, as shown in FIGS. 17 and 18. The blood pump 316, during operation, is preferably adapted to be within three feet of where the transseptal cannula 12 and the perfusion cannula are positioned to enter the patient. Preferably, the blood pump mechanism 30 includes tubing 324 which connects the blood pump 316 to the transseptal cannula 12 and the perfusion cannula 100 and the clamping mechanism clamps the tubing 324 between the blood pump 316 and the transseptal cannula 12. The tubing 324 has a continuous smooth inner surface 326.

Alternatives of the tubing 324 include:

a piece of tubing that connects the transseptal cannula to the pump inlet port and a piece of tubing that connects the arterial cannula to the pump outlet port, a quick connection device with a seamless connection (smooth without a step) to minimize the potential for thrombus formation and a lock mechanism to avoid inadvertent disconnection that can directly connect the transseptal and arterial cannulae to the pump, tubing integrals on the transseptal and arterial cannulae which can be placed over the barbs of the inflow and outflow ports of the pump and can be secured with a clamping mechanisms to the barbs at the pump inlet and outlet ports.

Figure 14:
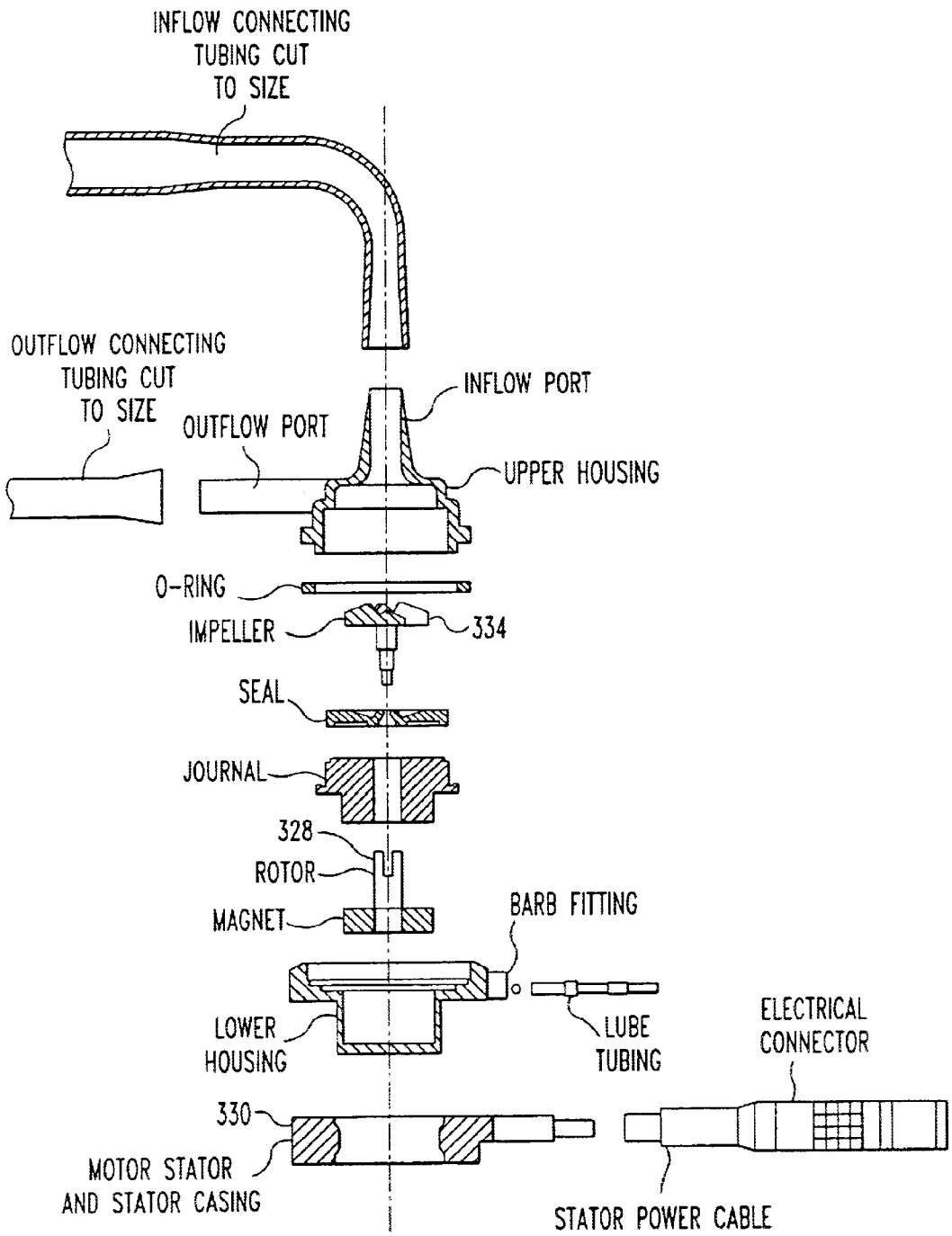
FIG. 14 is a schematic representation of the pump assembly.
Figure 15:
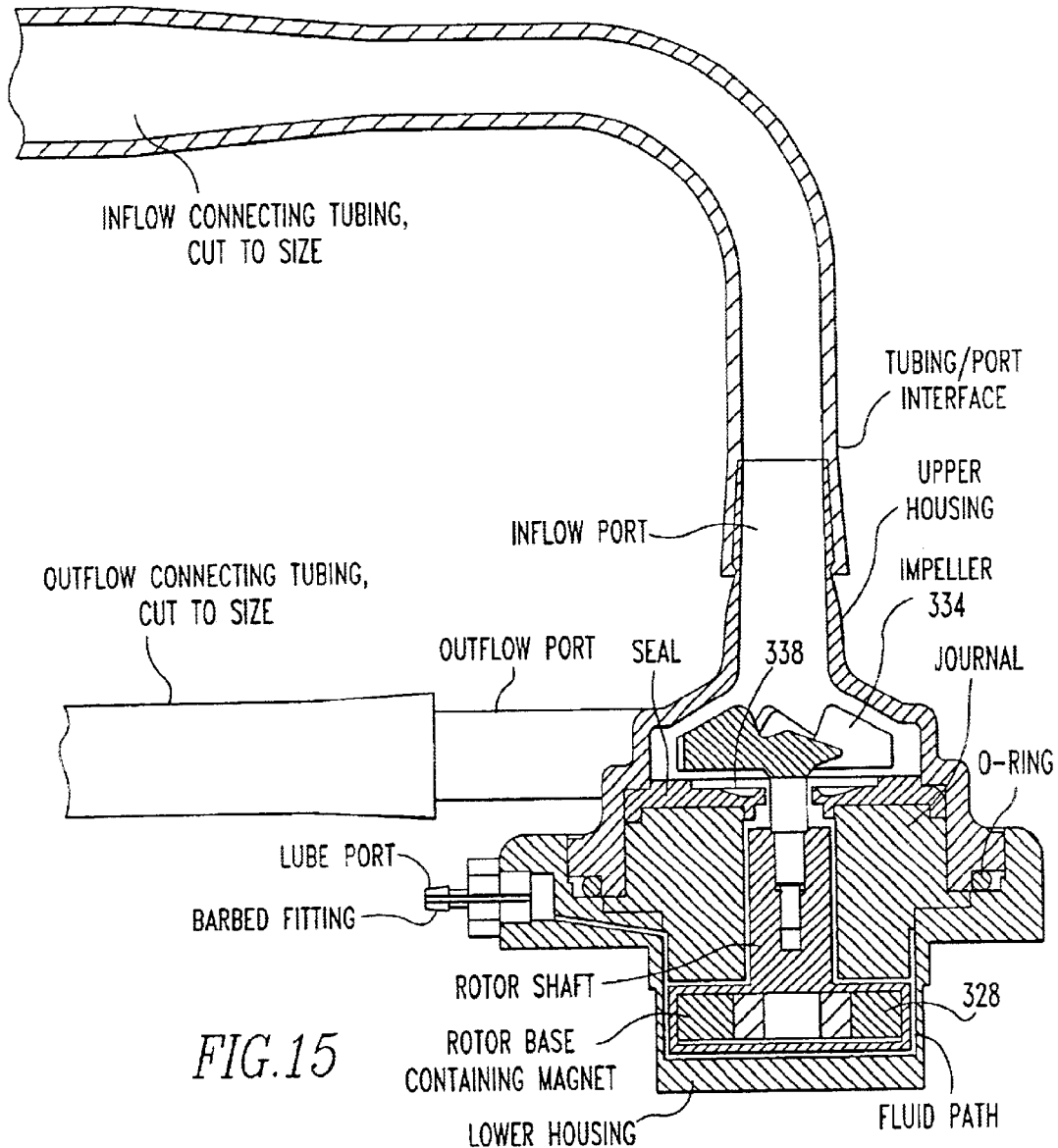
FIG. 15 is a schematic representation of a cross-sectional view of the pump.

Preferably, the blood pump 316 pumps a continuous flow of blood. The blood pump 316 preferably has a rotor 328 and a stator 330, as shown in FIGS. 14 and 15. Preferably, the blood pump mechanism 30 includes a controller 332 connected to the blood pump 316 through which the operation of the blood pump 316 is adjusted, as shown in FIGS. 16a, 16b, 16c, 16d and 16e. The blood pump 316 includes an impeller 334 which moves against the blood, and the user adjusts the operation of the blood pump 316 by changing impeller 334 speed. Preferably, the controller 332 measures flow of blood from the pump only from impeller 334 speed and stator 330 current. Alternatively, the blood pump mechanism 30 includes an electromagnetic or ultrasonic flow probe 336 in communication with the blood pump 316 and the controller 332 measures flow of blood through the pump with the electromagnetic or ultrasonic flow probe 336, as shown in FIG. 17.

Preferably, the pump has a hydrodynamic bearing 338 between the rotor 328 and the lower housing 330, shown in FIG. 15. The blood pump mechanism 30 preferably includes a fluid reservoir 340 and a fluid pump 342 connected to the fluid reservoir 340 and the blood pump 316 to pump fluid to the hydrodynamic bearing 338 in the blood pump 316. Preferably, the fluid reservoir 340 includes predetermined concentrations of drugs. See U.S. Pat. No. 5,711,753 for a more complete discussion of the pump 316, incorporated by reference herein, except the occluder described therein is not needed in the extracorporeal application.

The pump controller 332 preferably provides current to the blood pump 316 and the controller 332 includes a battery 344 that provides energy to run the controller 332 and the blood pump 316. The battery 344 is used for powering the blood pump 316 and controller 332 when the patient is being moved between remote locations. Preferably, the blood pump 316 is made of biocompatible materials which have no effect on blood or the patient. See the Appendix. The blood pump 316 is preferably a centrifugal pump or an axial pump. Alternatively, a pulsatile flow may be obtained by modulation of pump speed through controller 332 and synchronizing impeller speed variation with the patient's beating heart.

Alternatively, the blood pump 316 is a pulsatile, electrical or pneumatic pump having an inflow valve and a perfusion valve. Farrar, D. J., Compton, P. G., Lawson, J. H., Hershon, J. J., Hill, J. D., "Control Modes of a Clinical Ventricular Assist Device". *IEEE Engineering in Medicine and Biology Magazine*, pp. 19–25, vol. 5, 1986, incorporated by reference herein. Preferably, the blood pump mechanism 30 includes a controller 332 connected to the blood pump 316 through which the operation of the blood pump 316 is adjusted. The pump is preferably a pulsatile pump having a stroke time, and the controller 332 adjusts the operation of the blood pump 316 by adjusting stroke time. Preferably, the pump controller 332 provides current to the blood pump 316 and the controller 332 includes a battery 344 that provides energy to run the controller 332 and the blood pump 316, the battery 344 is used for powering the blood pump 316 and the controller 332 when the patient is being moved between remote locations.

Preferably, the system 300 includes a holding mechanism 346 which holds the blood pump 316 and attaches to the patient, as shown in FIGS. 18–23. The holding mechanism 346 preferably includes a pump holding portion 348 which holds the pump and a patient portion 350 which is adapted to fit to the leg 352 of the patient and to secure to the pump holding portion 348. Preferably, the pump holding portion 348 is made of plastic having an imprint 352 of the shape of the blood pump 316 in which the blood pump 316 fits to be held by the pump holding portion 348, and the patient holding portion 348 includes a band 354 with loops and with straps 356 having hooks adapted to wrap about the leg 352 and the pump holding portion 348 to hold the pump holding portion 348 to the leg 352. The holding mechanism 346 is preferably adapted to attach to either leg 352 of the patient and allow inflow or outflow to be connected to the contralateral side of the patient. Preferably, the holding mechanism 346 is adapted to hold the blood pump 316 in a normal position or at an angle of 20 degrees from the normal position.

The present invention pertains to a method for assisting flow of oxygenated blood. The method comprises the steps of inserting percutaneously in the femoral vein of the patient and extending through the atrial septum from the right atrium to the left atrium a transseptal cannula 12. Next there is the step of inserting percutaneously in the femoral artery a perfusion cannula 100 for returning oxygenated blood to the arterial system 300 of the patient. Then there is the step of pumping blood with a blood pump 316 connected to the transseptal cannula 12 and the perfusion cannula 100 at specified flow rates over a range of physiological pressures with performance monitoring to offer fault tolerance and management.

The Transseptal Cannula Set Contains:

1–21 Fr. Percutaneous Venous Transseptal Cannula (PVTC)

1–13 Fr. Percutaneous Venous Transseptal Catheter

1–14/21 Fr. Percutaneous Venous Transseptal Two Stage Dilator

The following instruments are needed to complete the procedure and should be supplied by the user (all are standard in the art):

Introducer Needle

Guidewire, super stiff, 0.035 in., at least 260 cm long.

Transseptal Puncture Kit

Transseptal Catheter/Dilator (as needed).

Figure 27A:
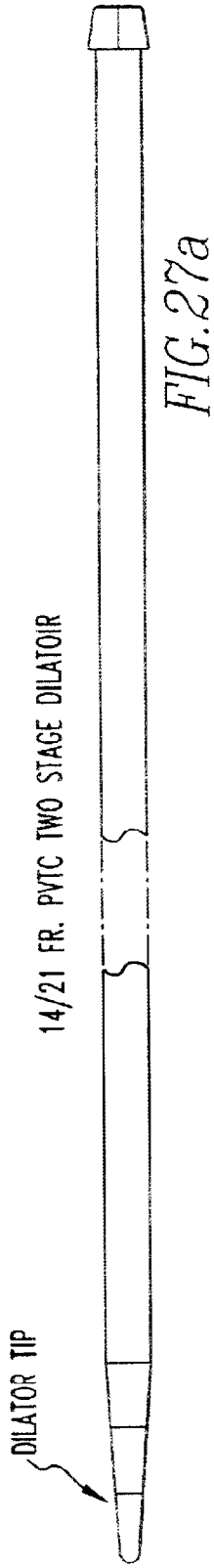
FIGS. 27a–27c are schematic representations of the components of the cannula set.
Figure 27B:
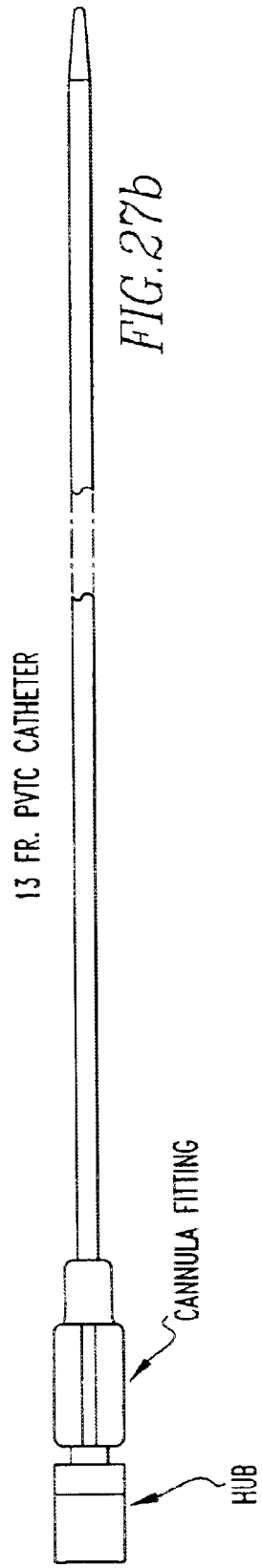
Figure 27C:
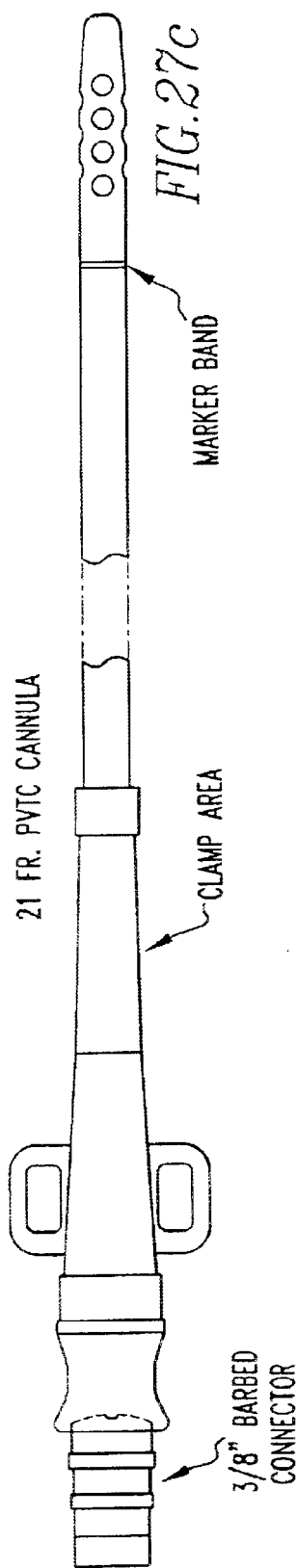

Components of the cannula set are shown in FIG. 27.

The transseptal cannula is inserted in the following manner:

Prior to performing the procedure, insert the PVTC Catheter into the PVTC Cannula assuring that the Cannula fitting on the Catheter fits snugly and is fully inserted into the ⅜ in. barbed connector of the Cannula. Assure that the tip of the Catheter is extended fully from the Cannula.

Use standard transseptal puncture technique to gain access into the left atrium from the femoral vein.

Dilate the transseptal puncture site (fossa ovalis) with a transseptal puncture catheter in the usual manner.

Introduce the 0.035 in. guidewire into the left atrium. Verify that the guidewire is in position in left atrium.

Verify patient ACT is in excess of 400 seconds.

Remove the transseptal puncture catheter.

Advance the Two Stage Dilator over the guidewire into the left atrium to dilate the fossa ovalis. Monitor progress using fluoroscopy to assure that the tip does not penetrate the atrial chamber.

Remove the Two Stage Dilator.

Advance the PVTC Catheter/Cannula assembly over the guidewire into the left atrium.

Position the PVTC Cannula tip in the left atrium using fluoroscopy. Assure that all of the drainage holes are in the left atrium and the marker band is near the septum.

Remove the guidewire and Catheter together to allow the cannula to be back filled with blood.

Clamp the adapter of the PVTC Cannula on the clamping area of the clear adapter.

The arterial cannula is inserted in the following manner:

Introduce an arterial guidewire into the artery location chosen.

Advance the arterial cannula over the guidewire into the artery.

Verify the blood is arterial blood.

Remove the guidewire.

Clamp the cannula to prevent blood loss prior to connection to the blood pump.

The extracorporeal circuit is connected to the pump in the following manner:

Connect appropriate length standard ⅜ in. extracorporeal blood circuit tubing to the inflow and outflow ports of the Pump.

Connect the inflow tubing to the inflow cannula.

Release the inflow cannula clamp and prime the Pump and outflow tubing with blood. Clamp the outflow tubing ensuring no air between the inflow cannula and the clamp on the outflow tubing.

Make a wet to wet connection of the outflow tubing and the outflow cannula.

If there is a vent on the outflow cannula, aspirate any final air from the extracorporeal blood circuit.

If there is no vent on the outflow cannula, inspect the extracorporeal circuit for air. If there is any air, break and remake the wet to wet connection of the outflow tubing and outflow cannula until all of the air is purged from the extracorporeal blood circuit.

Secure all tubing connections with sta-straps.

Release the hemostat on the outflow tubing followed by the hemostat on the inflow cannula.

Adjust pump speed to desired setting and place Pump in Mounting Assembly and secure to patient's leg.

Preferably, before the pumping step, there is the step of clamping a transseptal clamp mechanism 322 to the transseptal cannula 12 and the blood pump 316 to avoid undesired disconnection of the blood pump 316 and the transseptal cannula 12. Before the pumping step, there is preferably the step of positioning the blood pump 316 within three feet of where the transseptal cannula 12 and the perfusion cannula 100 are inserted into the patient.

Preferably, the pumping step includes the step of pumping a continuous flow of blood with the blood pump 316. Preferably, the pumping step includes the step of adjusting the flow of blood pumped with a controller 332 connected to the blood pump 316. The adjusting step preferably includes the step of adjusting impeller 334 speed of an impeller 334 of the blood pump 316 to attain a desired flow of blood in the patient due to the operation of the blood pump 316. Preferably, after the pumping step, there is the step of powering the controller 332 and the blood pump 316 with a battery 344 as the patient is moved from a first location to a second location remote from the first location.

Before the pumping step, there are preferably the steps of attaching a holding mechanism 346 for the blood pump 316 to the patient and placing the blood pump 316 in the holding mechanism 346 to hold the blood pump 316 in place relative to the patient. Preferably, the attaching step includes the step of attaching the holding mechanism 346 to the leg 352 of the patient. The placing step preferably includes the step of wrapping straps of a band 354 positioned about the leg 352 of the patient, about the blood pump 316, and fixing hooks 360 of the straps to loops 358 of the band 354 to secure the blood pump 316 to the leg 352 of the patient.

Alternatively, the pumping step includes the step of pumping pulses of blood through the patient with a pulsatile pump. The pumping step then can include the step of adjusting stroke timing of the pulsatile pump to obtain the desired pulse of blood flow through the patient.

Figure 1:
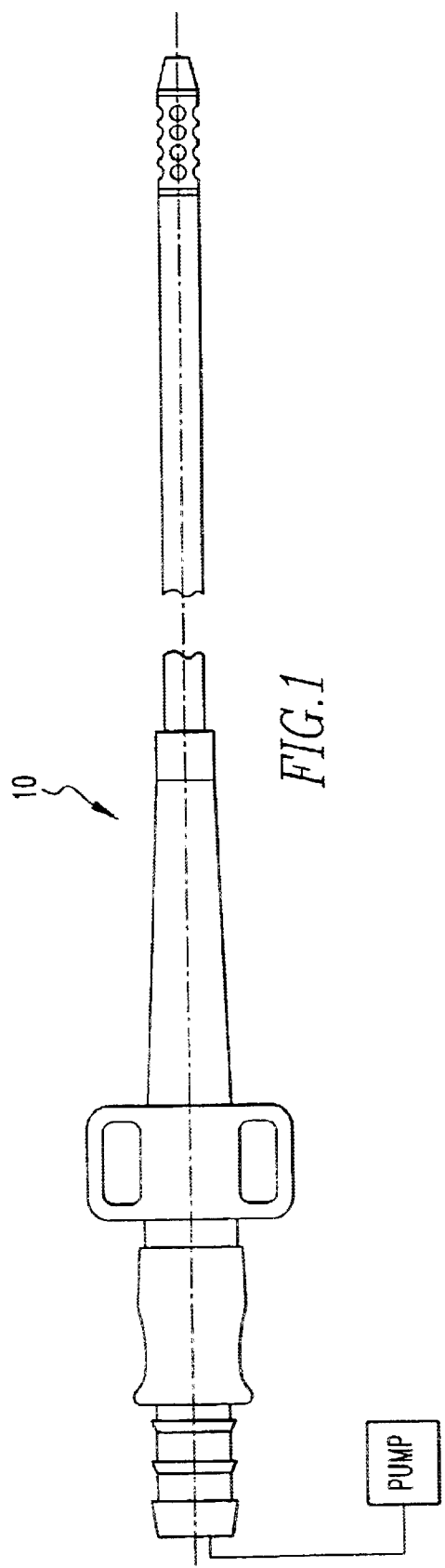
FIG. 1 is a schematic representation of the transseptal cannula portion of the present invention.
Figure 2:
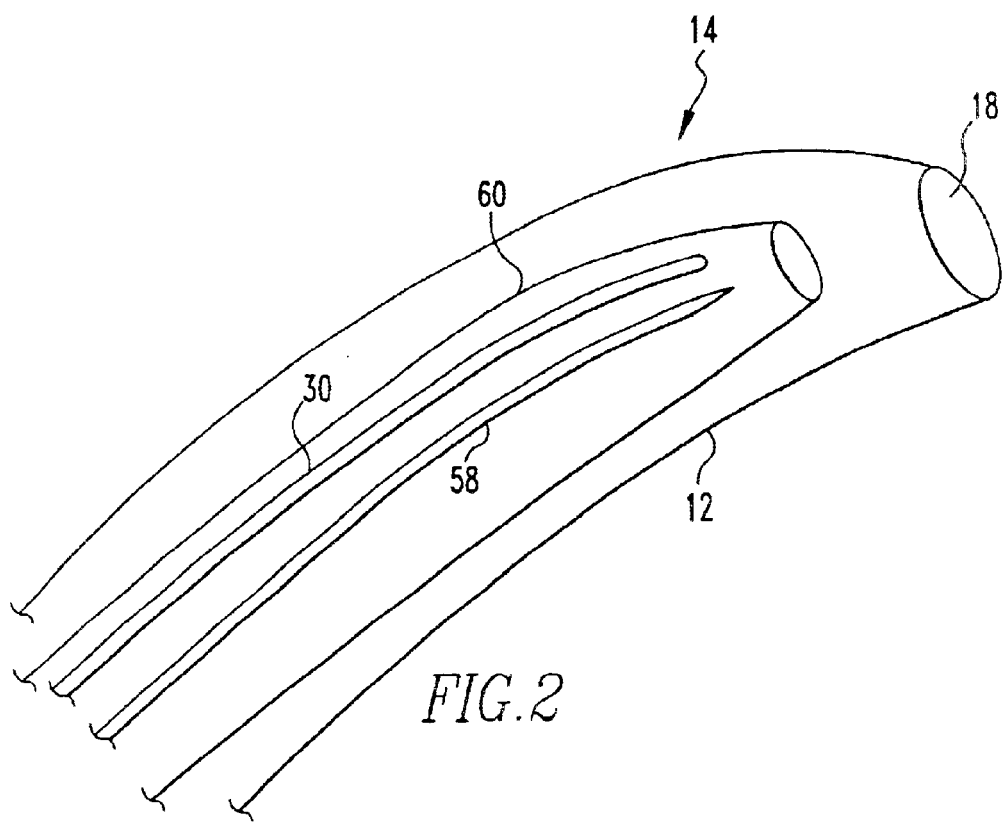
FIG. 2 is a schematic representation of a needle and wire in a second catheter in a cannula.
Figure 3:
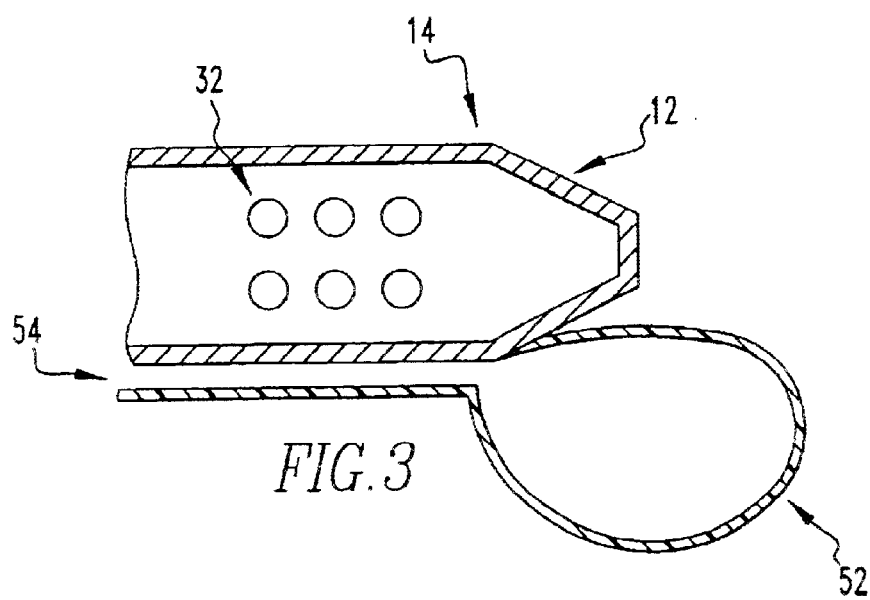
FIG. 3 is a schematic representation of a balloon catheter at the distal end of the cannula.

In the operation of the invention, and referring to FIGS. 1, 2 and 3, the distal end 14 of the transseptal cannula 12, is inserted into a patient and moved to the right atrium of the patient's heart via the femoral vein, as is well known in the art. Generally, this occurs in the following way. The guide wire 30 is introduced into the patient and threaded to the right atrium of the patient. The cannula 12, the second catheter 60 (with the needle 58 disposed in the second catheter 60) are placed over the end of the guide wire 30 extending from the patient via the orifice 18 and the opening in the second catheter 60. The cannula 12 and second catheter 60, with the needle 58 inside the second catheter 60, are then inserted and moved along the guide wire 30 to the right atrium of the patient. When the distal end 14 of the cannula 12 is in the right atrium, the guide wire 30 is pulled back 46 into the cannula 12 freeing the orifice 18 so there is nothing in the orifice 18. The needle 58 is then advanced, as is the second catheter 60 through the orifice 18 so the second catheter 60 extends through the orifice 18 of the cannula 12 and the needle 58 extends through the opening of the second catheter 60. The needle 58 and second catheter 60 are then forced into the septum until they puncture the septum and move into the left atrium. The needle 58 is then retracted from the opening of the second catheter 60 and the guide wire 30 is moved forward through the second catheter's opening into the left atrium. The second catheter 60 is maintained in position while the guide wire 30 is maintained in place in the left atrium. The cannula 12 is then advanced forward into the left atrium along the guide wire 30 and the second catheter 60 which extend through the orifice 18. The presence of the second catheter 60 acts as a stiffener for the cannula 12 to assist in the placement of the cannula 12 in the left atrium. The second catheter 60, needle 58 and guide wire 30 are then removed from the cannula.

Preferably, the transseptal cannula 12 connection step includes the step of connecting the transseptal cannula 12 to the tubing 324 connected to the blood pump 316. Preferably, prior to clamping the clamping mechanism 322 to connect the tubing 324 to the transseptal cannula 12, there are preferably the steps of filling the transseptal cannula 12 with blood and confirming proper transseptal cannula 12 position by visualizing blood color, as is well known in the art.

It should be noted that the aforementioned procedure can be performed without the introducer catheter. Instead, the second catheter 60 acts with a dual purpose, as the introducer catheter and the second catheter 60. In this case, the needle 58 and guide wire 30 are together inserted in the second catheter 60, and the introducer catheter is not present. When the second catheter 60 and needle 58 puncture the septum and move into the left atrium, the second catheter 60 remains in place and the guide wire 30 and the needle 58 are removed to clear a blood flow passage through the second catheter 60. This apparatus of second catheter 60, guide wire 30 and needle 58, without any of the other features described herein on the cannula 12, or with some or all of them, in and of itself can be used to access the left atrium. Again, the advantage of the combination of elements, is that it can serve to access the left atrium without having to take turns pulling the guide wire 30 out and then inserting the needle 58 into the second catheter 60 since the guide wire 30 and the needle 58 are together present in the second catheter 60 simultaneously; and the second catheter 60 serves a dual purpose of being the introducer catheter and second catheter 60, without needing the introducer catheter. Alternatively, the needle can be inserted into the second catheter 60 after the second catheter has reached the right atrium.

During the process of moving the cannula 12 to the right atrium, removing the guide wire 30 from the orifice 18 and extending the needle through the orifice 18, an imaging device, external to the patient is imaging the location of the orifice 18 (and during the entire procedure) by noting where an end marker 34, disposed about the orifice 18, is located in the patient. Such an imaging system, for instance with the end marker 34 being radio opaque, is well known in the art. If it is desired, the guide wire 30 or a portion thereof, such as the tip of the guide wire 30, and/or the needle 58 or a portion thereof, such as the tip of the needle 58, can also be enhanced for imaging purposes, for example by having a radio opaque material, so the guide wire 30 and needle 58 can also be followed as they move through the patient.

Figure 8:
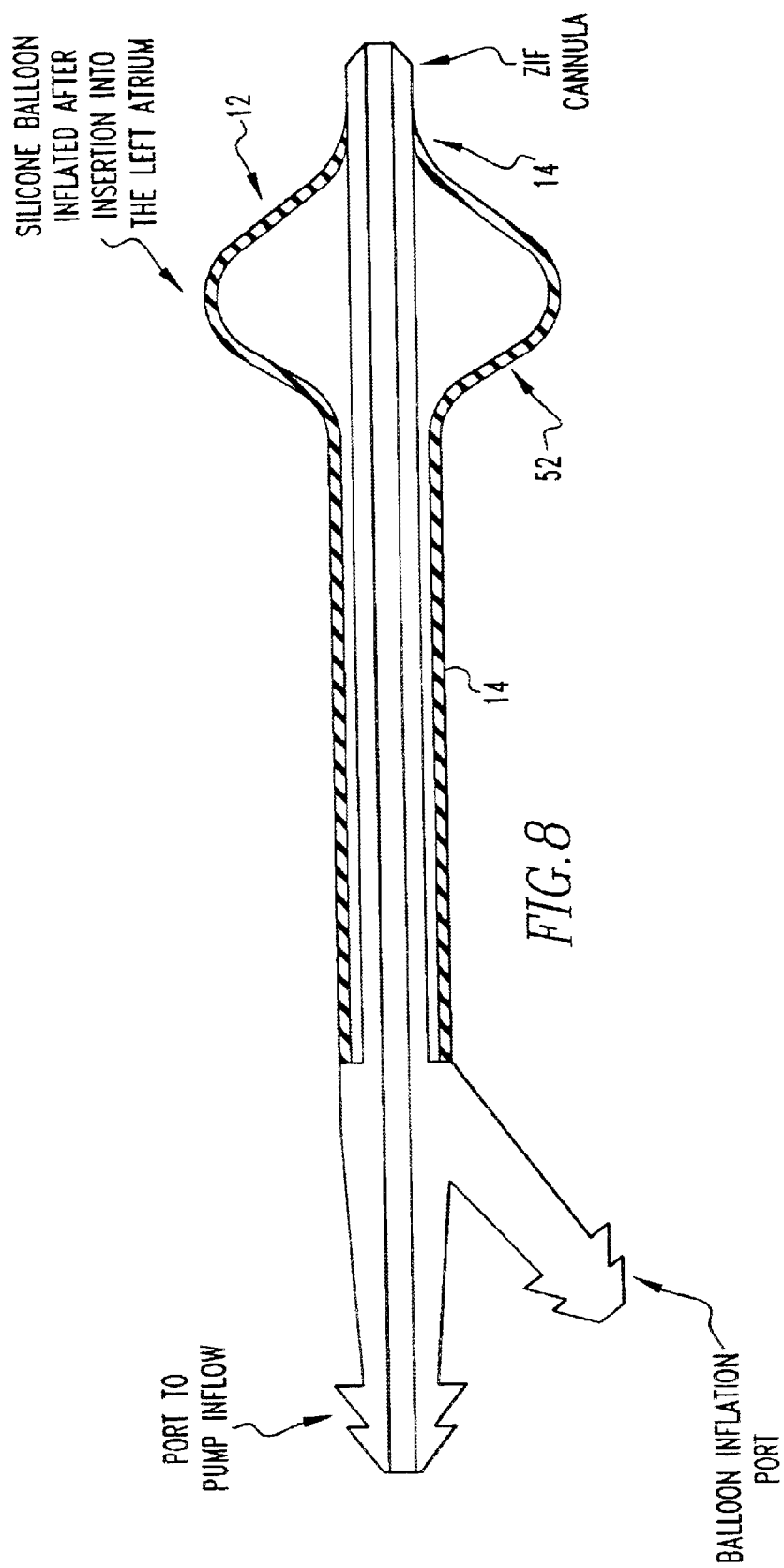
FIG. 8 is a schematic representation of an alternative embodiment of a balloon at the distal end of the cannula.

Once the orifice 18 is positioned in the left atrium and the port 20 of the cannula 12 is positioned in the right atrium, a balloon 52 disposed adjacent the orifice 18 is inflated with saline, as shown in FIG. 3, which travels along an inflation tube 54 that runs the length of the cannula 12 along the outside of the cannula 12 to a saline supply 87 disposed outside of the patient. The inflated balloon 52 serves to prevent the distal end 14 of the cannula from puncturing an atrium wall 50 of the left atrium where the distal end 14 of the cannula is now disposed, for instance when the patient is being turned or moved. The inflated balloon 52 also serves to prevent the cannula 12 from slipping back into the right atrium at undesired times, such as when the patient is being turned or moved about. The balloon 52 can be deflated by removing the saline that has been introduced into it through the inflation tube 54, back out of the inflation tube 54 with negative pressure applied to the end of the inflation tube 54 extending externally from the patient. In another embodiment of a balloon 52 with the cannula 12, as shown in FIG. 8, the balloon 52 is disposed at the distal end 14 of the cannula 12.

Figure 4:
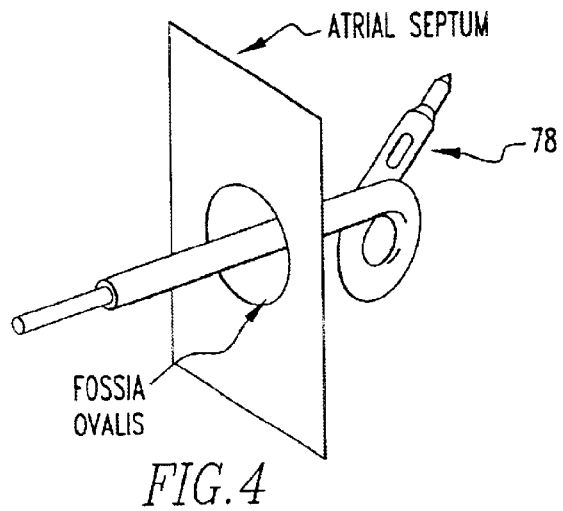
FIG. 4 is a schematic representation of a pigtail cannula.
Figure 5:
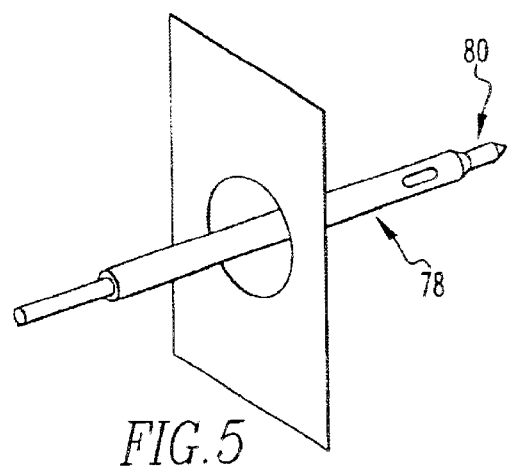
FIG. 5 is a schematic representation of a pigtail cannula with a straightening dilatory.

Alternatively, a pigtail cannula 78, as shown in FIG. 4, can be used which has its distal end curling about. As long as a straightening dilator 80 or needle 58 is present in the pigtail cannula 78, the pigtail cannula 78 is straight, as shown in FIG. 5. As soon as the dilator 80 is removed, the pigtail cannula's distal end curls about to achieve the same results as the inflated balloon 52. See U.S. Pat. No. 5,190,528 titled "Percutaneous Transseptal Left Atrial Cannulation System" by James D. Fonger et al. and PCT patent application number PCT/US00/13601, incorporated by reference herein, for further information about a transseptal cannula and its use.

Figure 6:
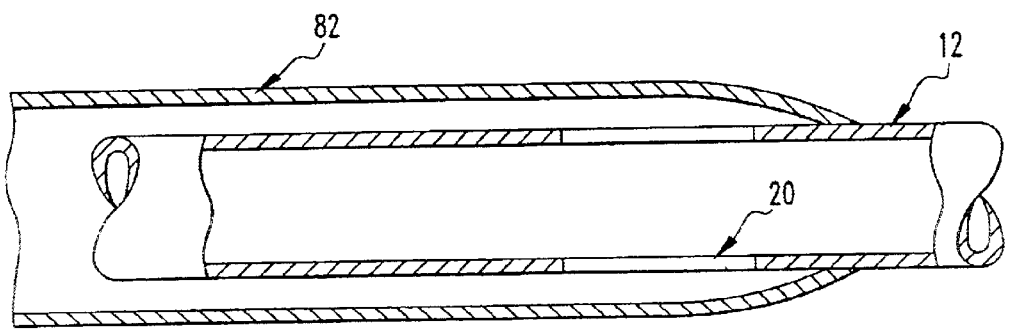
FIG. 6 is a schematic representation of a transseptal sheath over the port of a cannula.
Figure 7:
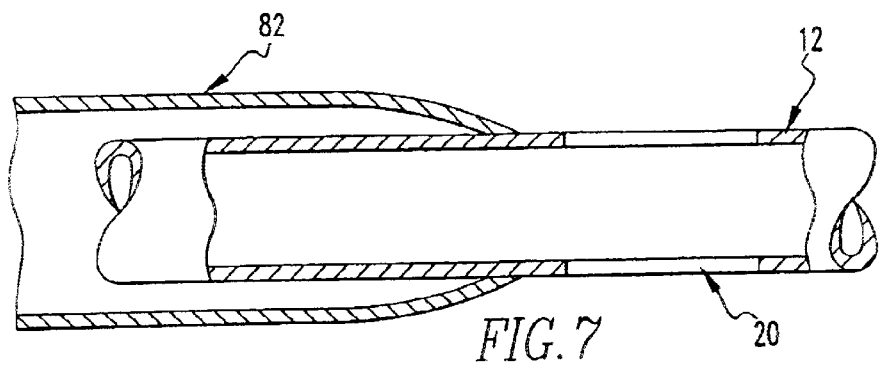
FIG. 7 is a schematic representation of the transseptal sheath retracted from the port of the cannula.

Alternatively, a transseptal sheath 82 positioned about the cannula 12 can be used, as shown in FIG. 6. When the transseptal sheath 82 is in a closed position, it covers over the port 20 so no blood can pass through the port 20. When the transseptal sheath 82 is in an open position, meaning it has been retracted by being pulled on from outside the patient, the transseptal sheath 82 has moved away from the distal end 14 exposing the port 20, as shown in FIG. 7. The extent the transseptal sheath 82 has been retracted determines how much of the port 20 is exposed. The transseptal sheath 82 can also have a marker at its end, and the cannula 12 can have gradations which are marked to identify where the end of the transseptal sheath 82 is relative to the cannula 12.

Holes 32 having an elongate shape and disposed essentially in parallel with the axis of the cannula 12 and between the orifice 18 and the port 20 further facilitates movement of blood into and out of the cannula 12. The elongate shape of the holes 32 minimizes damage to the cellular structure of the blood cells as they pass through the holes 32. Furthermore, all openings, such as the orifice 18 and the port 20, are made as smooth as possible and are made of bio-inert materials such as plastic or steel to minimize or preclude the clotting of blood. In this way, access to the left and right atriums of the patient is achieved for whatever purpose, such as the attachment of a pump to the cannula 12.

Figure 9:
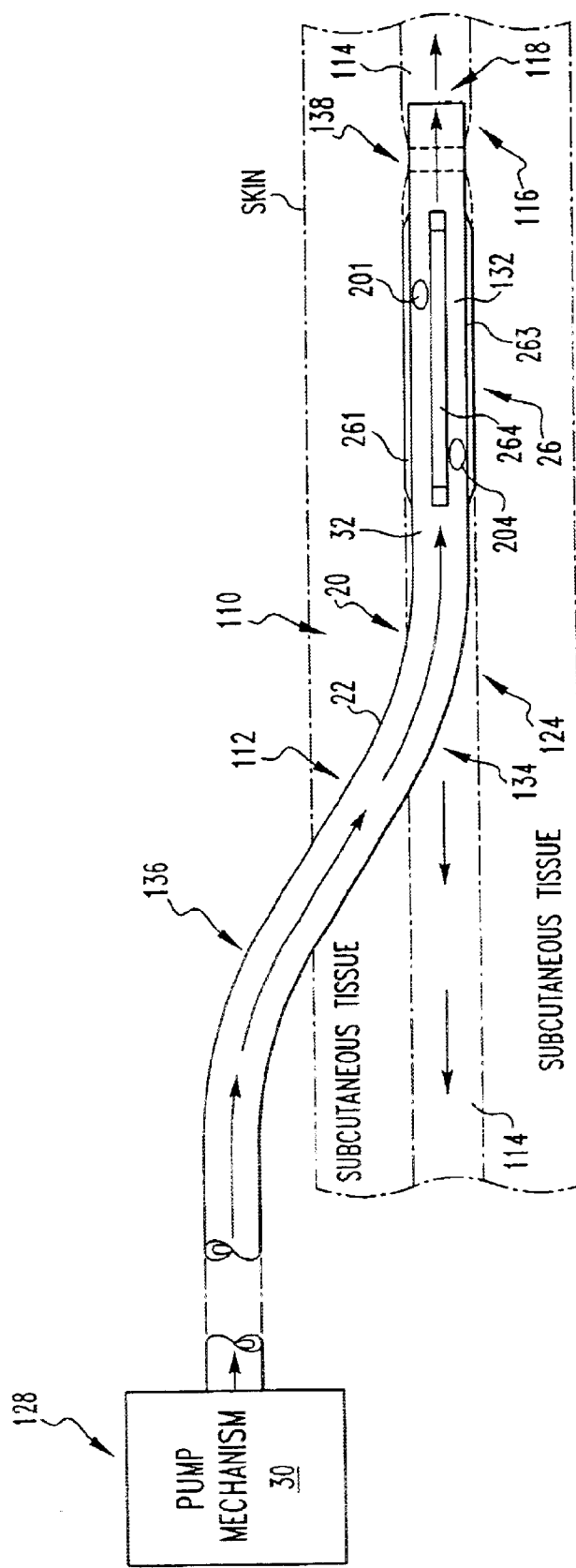
FIG. 9 is a schematic representation of the arterial connection system of the present invention.
Figure 10:
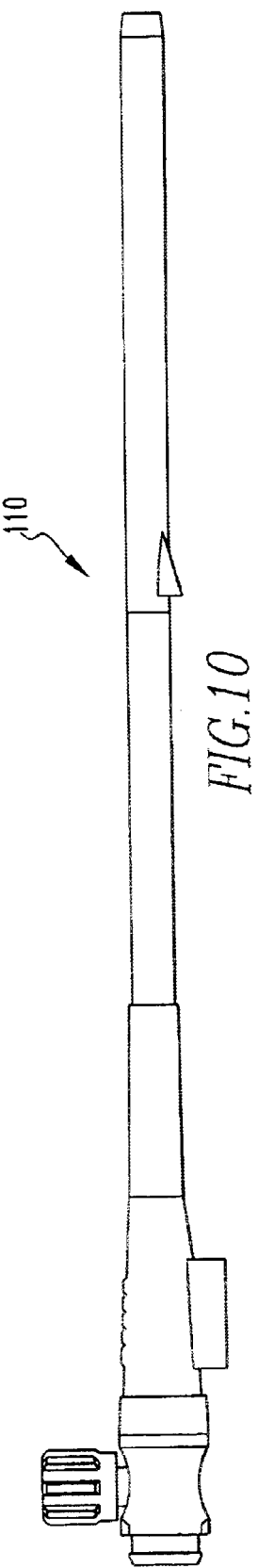
FIG. 10 is a schematic representation of an alternative arterial perfusion cannula of the present invention.

The perfusion cannula 100 connected to the pump mechanism 30, as shown in FIG. 9, is inserted into the femoral artery of a patient 50 the distal end 116 of the tube 112 of the perfusion cannula 100 is disposed in the femoral artery, as is well known in the art. See U.S. Pat. No. 5,330,433 titled "A Bidirectional Femoral Arterial Cannula" by James D. Fonger et al. and U.S. patent application Ser. No. 09/400,800, incorporated by reference herein, for further discussions and use of a perfusion cannula.

Preferably, the perfusion cannula 100 connection step includes the step of connecting the perfusion cannula 100 to the tubing 324 connected to the blood pump 316. Preferably, the connection step includes the step of priming the perfusion cannula 100. Preferably, prior to clamping the clamping mechanism 322 to connect the tubing 324 to the perfusion cannula 100, there is the step of filling the perfusion cannula 100 with oxygenated blood.

Selecting the size of perfusion cannula depends on patient's body size. A bigger size of perfusion cannula can allow higher blood flow rate and thus unloading the patient's heart better. However, if the perfusion cannula size is too big, the cannula may block the blood stream through patient's leg. It is desirable to choose an appropriate perfusion cannula size such that the total blood flow rate through the cannula between 1 and 4 L/min, preferably 1 to 3.5 L/min. In addition, the blood stream through patient's leg between femoral artery and the perfusion cannula should have the flow rate between 100 ml/min and 500 ml/min, preferably 200 ml/min to 400 ml/min.

Prior to pump attachment, the two chambers (upper and lower) of the pump are primed to prevent air from being pumped into the patient after attachment to the other system components. The lower chamber uses fluid infusate to provide a bearing function that prevents motor wear, provides cooling, and provides anti-coagulation directly to the upper chamber, where blood flows during operation. First, the infusate line is primed with sterile infusate from the infusate supply system. The lower chamber, or motor chamber, is then filled with sterile infusate from the infusate line. A syringe is used to push fluid through the infusate system and into the lower chamber. The pump is then started, with the pumping action pulling all air through the seal separating the upper and lower chambers. Alternately, a syringe with two way stopcock can be used to suck air out of the lower chamber prior to filling with infusate. The upper chamber, or blood flow chamber, is filled with saline from either the inflow or outflow port. Owing to the low pump volume, this can be accomplished with saline.

Figure 13:
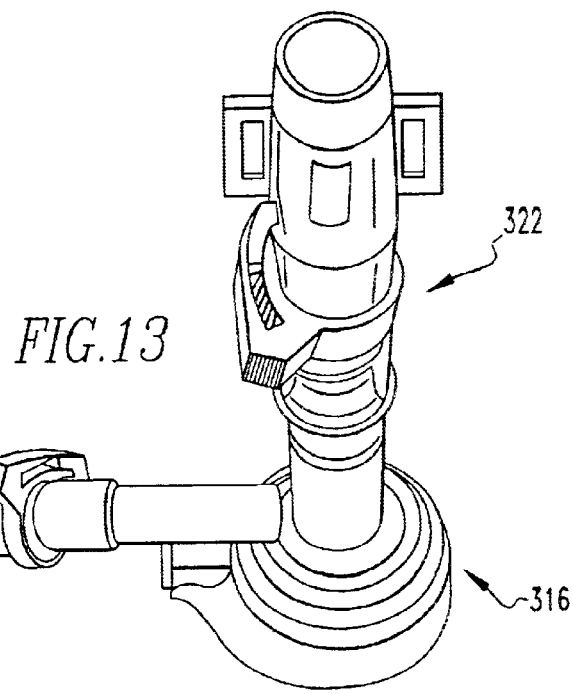
FIG. 13 is a schematic representation of the pump with the clamp mechanism.
Figure 12:
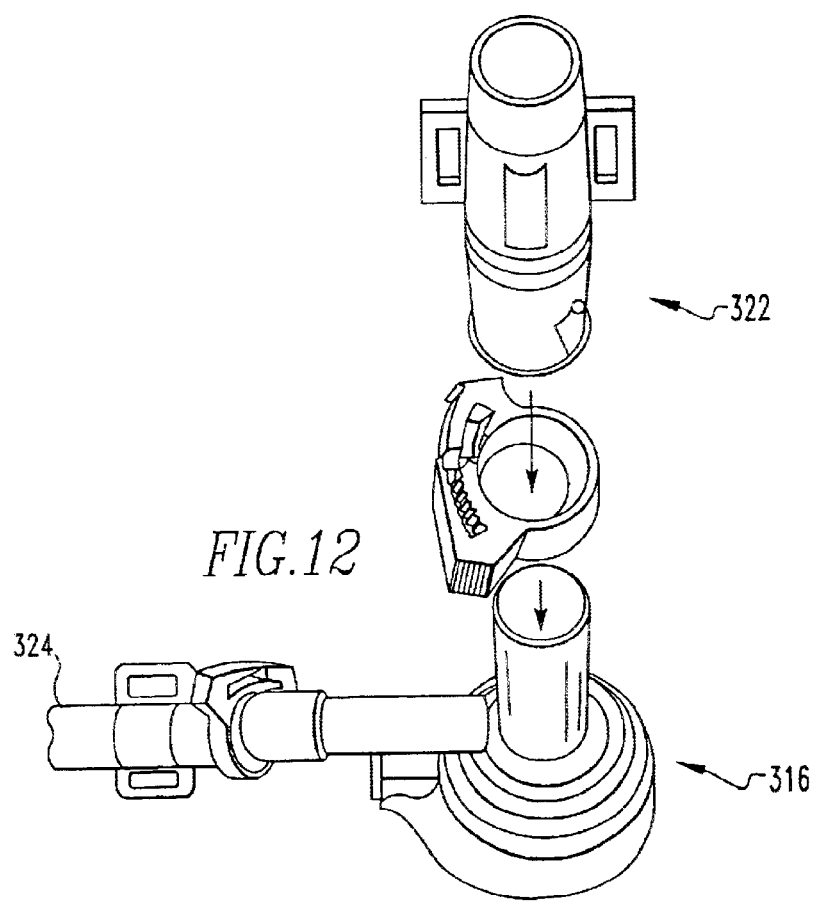
FIG. 12 is a schematic representation of an exploded view of the pump with the clamp mechanism.

Once the transseptal cannula and the perfusion cannula are in position in the patient, the blood pump 316 is connected to them, as shown in FIGS. 11–13. Connection of the blood pump 316 to the transseptal cannula and the perfusion cannula is accomplished with tubing 324 that extends between the input cannula of the blood pump 316 and the transseptal cannula, and the output cannula of the blood pump 316 and the perfusion cannula. The tubing 324 is secured in place by the clamping mechanism 322 that clamps the tubing to the respective elements. The clamping mechanism 322 is used to avoid inadvertent disconnection of the elements and the tubing and to prevent leakage of air into the system. The blood pump 316 is positioned in close proximity, within 3 ft. to the ends of the perfusion cannula and the transseptal cannula which extend from the patient to minimize the system blood volume and to minimize heat loss of the blood in the extracorporeal portion of the system. The tubing 324 from the perfusion cannula and the transseptal cannula is designed so there is no step transition from the pump housing to the connecting tubing that would tend to create areas of low blood flow.

The blood pump 316 is placed into an imprint 352 of the holding portion 348 which corresponds to the shape of the blood pump 316, as shown in FIGS. 18–23. The holding portion 348 is placed on a band 354 about the patient's leg 352. Straps 356 of the band 354 are then placed over the blood pump 316. Loops 358 on the straps 356 are connected to the hooks 360 on the band 354 to secure the straps 356 on the band 354, thus holding blood pump 316 securely to the patient. The holding mechanism 346 comprising the holding portion 348 and the band 354 can be attached to either of the patient's legs and allows for inflow or outflow cannulation to the side opposite the pump fixation to the leg. The holding mechanism can fix the blood pump 316 in a position normal to the leg of the patient, or rotated 20 degrees from the normal to the patient's leg.

The blood pump 30 is a continuous flow blood pump, electrical in nature and magnetically driven having a rotor 328 and a stator 330. The blood pump components are constructed from biocompatible materials suitable for blood contact for periods of up to 14 days.

The primary function of the pump mechanism 30 is to pump blood. The pump 316 provides a range of volumetric flow rates from 1 to 4 1/min. over a mean arterial pressure range of 60 to 100 mmHg with a minimum of 5 mmHg left atrium filling pressure in persons with body surface areas (BSA) between 1.2 and 2.7 sq. meters. This is accomplished by the regulated rotation of the impeller at speeds of 3000 to 7500 rpm.

Secondary functions of the pump mechanism 30 provided by the controller 332 include:

Provide a fluid bearing and localized heparin in the pump.
Provide a system to monitor the fluid bearing infusate supply.
Provide a system to monitor the blood flow rate through the pump 316.
Provide a system to power the device.
Provide a system to interface to user.
Provide a performance monitor and alarm system.
Provide a software-based control system.

Alarm conditions are detected by the CPU and communicated to the user through audible and visual alarms on the controller display.

For single system faults, when a monitored system parameter goes outside an acceptable operating range, an alarm condition is set and a standard alarm sequence is started. The alarm is first issued by turning on an audible alarm device, turning on a flashing red alarm LED and displaying one or more related alarm messages on the display.

In case of multiple alarms, each time a new parameter goes out of range, a new audible alarm and flashing indication are generated. The alarm list fills top to bottom, that is, a new alarm message is added to the bottom of the alarm list and earlier alarm messages maintain their position on the list. The operator may be able to mute the alarm and the flashing LED may become steady, depending on the alarms present. As alarm conditions are cleared, the related alarm message is removed from the display but the alarm LED remains light. Only when all alarm conditions have been cleared, the red LED turns off. If the number of simultaneous alarms exceeds the available lines on the display, normally 13, then no new alarms appear on the display until previous alarms clear. The audible alarm as well as the alarm LED are still activated in the event of a new alarm condition during a alarm message overflow.

All muted Alarms reactivate within 2 minutes if the alarm condition persists.

A type 1 alarm condition is an indication that some critical pump electrical parameter has gone outside the acceptable operating range. A standard alarm sequence is started and pump power is removed. The operator is able to mute the audible alarm but the light still flashes if a type 1 alarm is present.

Pump parameter checking only occurs when the pump is turned on but not start until after a brief delay to allow the pump speed to settle to the desired setpoint. Battery monitoring is always active.

Type 1 alarm messages will clears if a pump restart is attempted.

A type 2 alarm condition is a warning to the operator it that some system parameter is approaching or has produced an unacceptable operating condition. A standard alarm sequence is started but the pump is not stopped. The operator is able to mute the audible alarm and the red light will change from flashing to steady if no type 1 alarm is present. If the alarm condition is cleared either by the operator or natural circumstances, the alarm clears.

The blood pump has a hydrodynamic bearing 338 between the rotor and the lower housing. See FIGS. 14 and 15. A lubrication system is used for the bearing. The purpose of the lubrication system is to provide a fluid bearing to the internal components of the pump and to provide a localized concentration of heparin to the blood in the interior of the pump for prevention of thrombus formation.

Figure 15A:
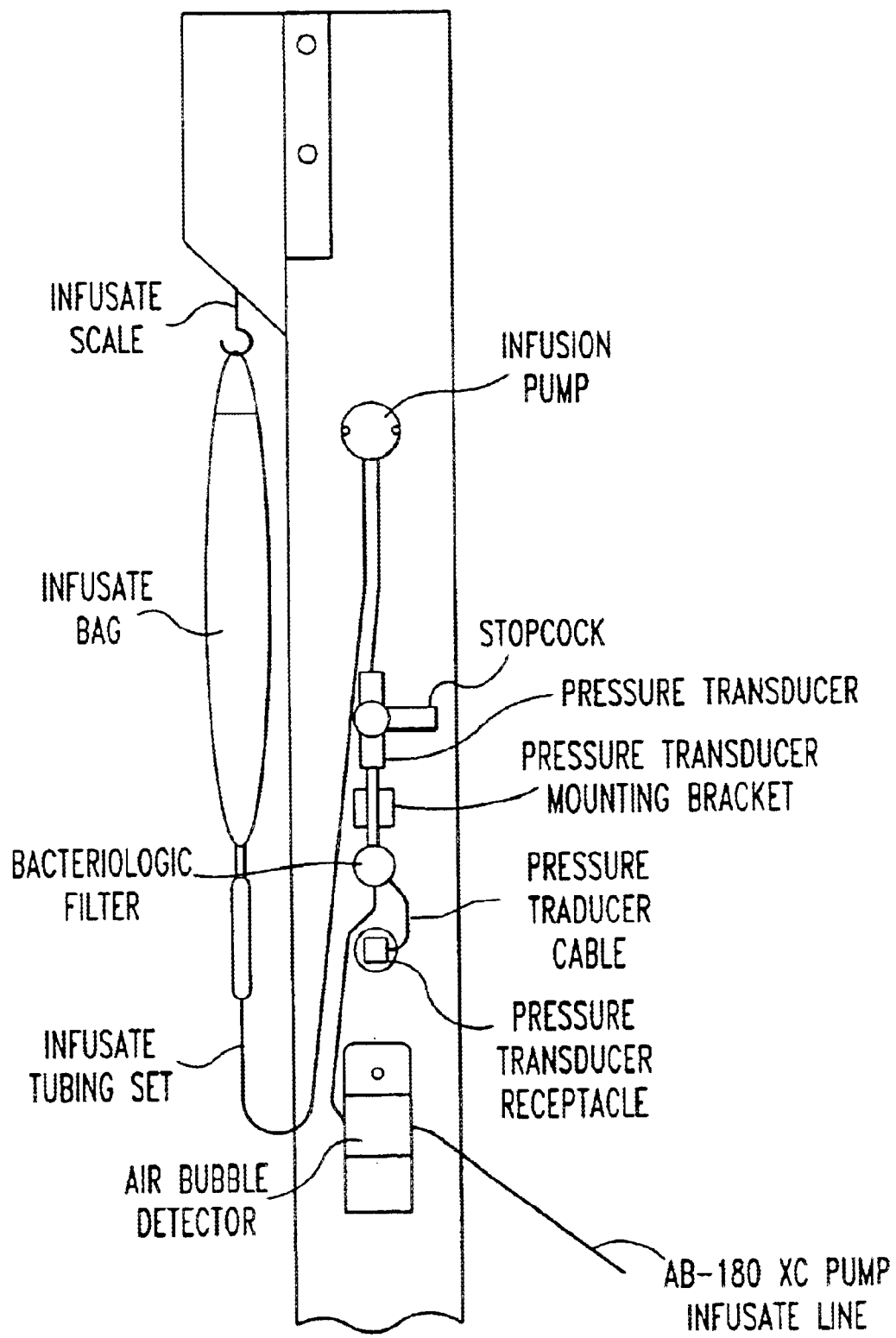
FIG. 15a is a schematic representation of the infusion system configuration.

Heparin is injected into a 1000 ml I.V. bag of sterile water (i.e., the infusate). The infusate flows through the I.V. set tubing, to the infusion tubing within the infusion pump in the controller. This infusion pump forces the infusate, at a constant rate of 10 ml/hr., through a bacteriologic filter, the 12 ft. of lube tubing in the external communicating line and into the lower housing as shown in FIGS. 15–15*a*.

The infusate in the lower housing flows between the rotor assembly and journal to provide a fluid bearing, thereby lubricating these components. The infusate flows from the lower housing through the center hole in the baffle seal and into the blood chamber. As a result of positive infusate fluid flow, blood will not pass below the seal into the lower housing. This infusate provides a localized source of heparin to the blood in the pumping chamber. This is shown in FIG. 15.

Blood pumps must not destroy red blood cells, must not cause clotting of the blood, and must locate and center themselves without offering a wear surface that can cause red cell damage or clotting over time. The location function must also prevent undesired contact between rotor and stator parts, which can cause pump heating, particulate accumulation in the blood, or pump seizure. The fluid bearing provides a force that aligns the rotating surface to be in the center of the stator, thus preventing contact. The closer the rotor and stator parts come to each other (as a result of electromagnetic forces due to motor operation or due to faults or inconsistencies in the components), the greater the force provided by the fluid, as generated by the flow and the geometries of the bearing surfaces. This centering force provides fail safe centering and location. The primary single point fault in this system is the loss of infusion flow, which is detected well in advance by the infusion management system, described elsewhere. If diluted with an anti-coagulant, the flow of this infusate also provides an anti-clotting mechanism directly to the pump blood chamber, where it is most needed. Without this anti-coagulation, the patient must be provided with a systemic anti-coagulation, which affects the clotting of all the blood in the patient. This carries the risk of internal bleeding. With the anti-coagulation involved with the infusion system of the AB-180 XC System, the concentration of anti-coagulation is large while it is in the blood chamber of the pump but is small by the time it is diluted with the other blood in the body. Therefore, the risk of internal bleeding associated with systemic anti-coagulation is negated.

The infusate supply is monitored by four distinct systems: 1) bag weigh system, 2) I.V. set drip chamber observation, 3) lube line pressure measurements, and 4) air detector. The purpose of the bag weigh system is to provide a monitoring and alarm system to alert the user of a low infusate volume condition because infusate flow is required for lubrication of the fluid bearing between the journal seal and the impeller shaft and to provide a constant infusion of heparin into the upper housing of the pump for localized anticoagulation.

A 1000 ml of sterile water containing 90,000 units of heparin provides 90 hours of operation before a warning alert is initiated. A large safety margin has been provided by designating a warning alarm to be sounded and displayed on the controller when the infusate volume remaining in the I.V. bag is 100±10 ml. This provides a maximum 10 hour interval before a run-dry condition could occur. A drip chamber has been provided in the design of the lubrication system so that visual checks can be made by bedside personnel that fluid is constantly leaving the infusate bag.

A third layer of protection is the warning alarm system based on the pressure measured in the lubrication system during pump operation. High and low pressure alarm warning limits provide safety by warning the operator that the lube line may have become disconnected (low pressure warning) or that the lube line may be kinked or the particulate bacteriologic filter has become clogged and needs to be changed (high pressure warning).

In order to mitigate the hazards associated with the infusion system and to manage the infusate delivery, a multi-alarm system has been implemented. This system is based on monitoring the infusion pump operation, monitoring pressure in the infusion line, and monitoring for any air, at the most downstream location that is practical, in the line.

Although the infusate flow rate is too low for conventional flow measurement techniques, infusion system operation can be confirmed considering the cyclical nature of the pressure in the infusion line downstream from the infusion pump. As the infusion pump rotates one full cycle, the pressure in the downstream line also cycles accordingly.

Figure 25A:
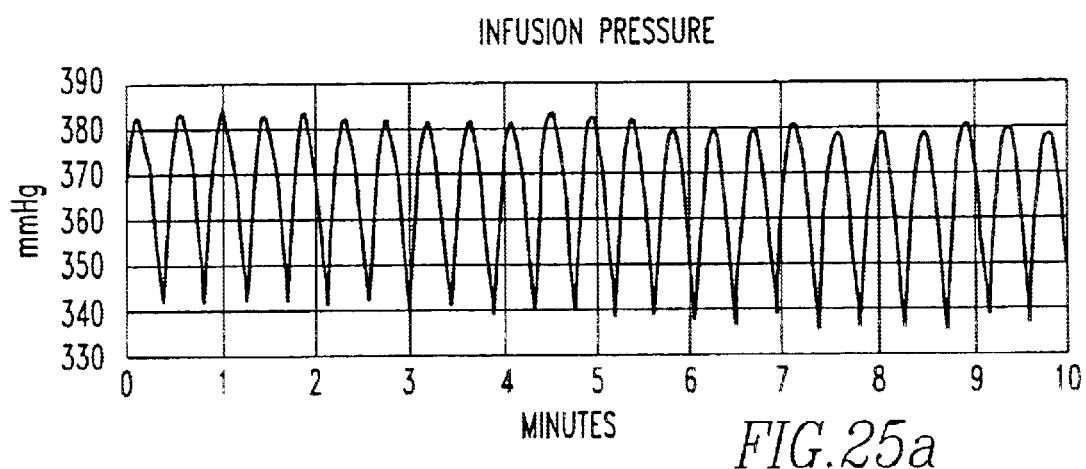
FIG. 25 is an illustration of pressure and pressure variation waveforms.
Figure 25B:
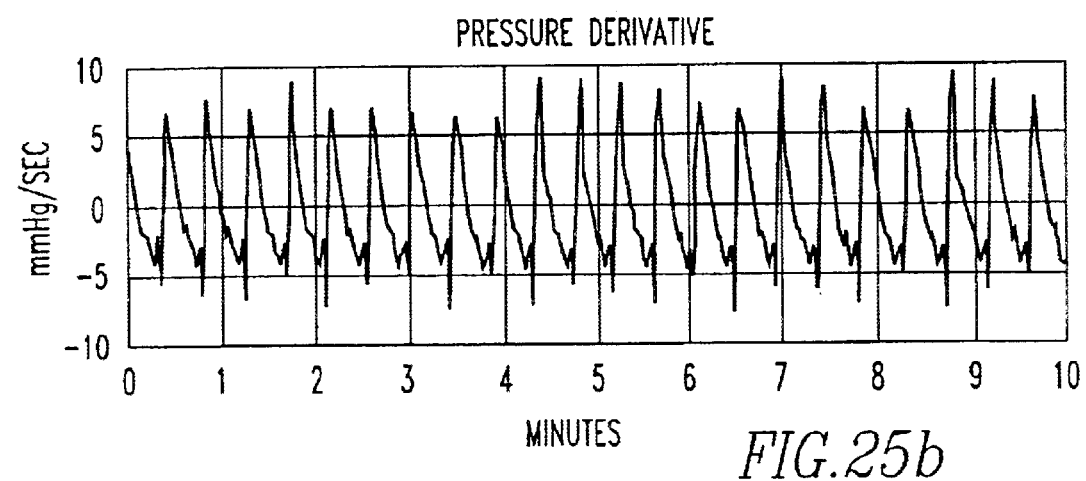

By measuring pressure in the downstream line, high pressure conditions can be monitored that would signal a kink or an occlusion in the line, and the frequency of pressure variation and the slope of that variation can be measured. The waveforms of pressure and pressure variation are shown in FIG. 25.

The frequency of the pressure variation within the infusion line is a measure of the speed of the infusion pump rotation, and it can be measured either by counting the number of zero crossings of the derivative of pressure or by measuring the time between consecutive zero crossings of pressure. The derivative of pressure is calculated as the difference in two discrete pressure measurements divided by the time between those measurements.

A high or low frequency of the pressure waveform indicates an infusion pump which is rotating faster or slower than normal, indicating an infusion flow rate which is out of specification.

The slope of the pressure variation is related to the infusate flow rate (i.e., below a specified limit) and can be used to detect a low flow condition. If the magnitude of dP/dt is 'low' for an extended period, then the infusate flow rate is considered to be low. Generally, this situation occurs when the infusion pump is pushing into an open line (constant, ambient pressure in the infusion line) or a kink in the line upstream to the infusion pump has stopped supplying fluid.

Specifically, alarms are generated by the infusion monitoring system under the following conditions:
HIGH INFUSION RATE
LOW INFUSION RATE
LOW LUBE FLOW (infusion pump stopped)
LUBE LINE OPEN (if air >=2 ul detected in the line).
LUBE OFFSET ERROR (see following discussion of pressure transducer).
LUBE PHASE SHIFT (if the time between successive zero crossings of derivative of the pressure is out of spec.)
LUBE PRESSURE HIGH
LUBE VOLUME LOW (if lube volume <90 ml, or 9 hours of infusate supply)
LUBE XDUCER REMOVED (if the perfusion system pressure transducer is removed)

Lubrication pressure is monitored at 1 second intervals. If a pressure above the high lube pressure limit is observed for 40±10 sec a standard alarm sequence is started and the LUBE PRESSURE HIGH message is displayed. If the alarm condition is observed not to occur for a continuous period of 2±10 sec or the LUBE PRESSURE LOW alarm condition occurs, the alarm clears. This alarm cannot occur when the lube transducer is disconnected. This alarm can occur prior to starting the pump.

Lubrication pressure shall be monitored at 1 second intervals. If a pressure lower than low lube pressure limit is observed for a continuous period of 40±10 sec while the pump is running, a standard alarm sequence is started and the LUBE PRESSURE LOW message is displayed. The alarm is not issued if the pump is stopped. If the alarm condition is observed not to occur for a continuous period of 2±10 sec or the LUBE PRESSURE HIGH condition occurs, the alarm clears. This alarm cannot occur if the lube transducer is disconnected. This alarm cannot occur unless the pump has been started at least once. This alarm does not occur in the "XD" version of the controller.

If the LOW LUBE FLOW condition is satisfied for 40±10 sec, while the pump is running, a standard alarm sequence is started and the LOW LUBE FLOW message is displayed. The alarm is not issued if the pump is stopped. If the alarm condition is observed not to occur for a continuous period of 40±10 sec or the HIGH INFUSION RATE condition occurs, the alarm clears. This alarm cannot occur when the lube transducer is disconnected or when the pump is off.

If the LOW INFUSION RATE condition is satisfied, while the pump is running, a standard alarm sequence is started and the LOW INFUSION RATE message is displayed. The alarm is not issued if the pump is stopped. If the alarm condition is observed not to occur for a continuous period of 10±1 min or the HIGH INFUSION RATE condition occurs, the alarm clears. This alarm cannot occur when the lube transducer is disconnected or when the pump is off.

If the HIGH INFUSION RATE condition is satisfied, while the pump is running, a standard alarm sequence is started and the HIGH INFUSION RATE message is displayed. The alarm is not issued if the pump is stopped. If the alarm condition is observed not to occur for a continuous period of 10±1 min or the LOW INFUSION RATE condition occurs, the alarm clears. This alarm cannot occur when the lube transducer is disconnected or when the pump is off.

Bag weight is monitored at 1 second intervals. If bag volume is observed to drop below the alarm threshold for 3 consecutive 1 second intervals, a standard alarm sequence is started and the LUBE VOLUME LOW message is displayed. The message is removed and the alarm cleared when the bag volume is greater than the alarm threshold for 3 consecutive 1 second intervals.

When a lube transducer is disconnected and then placed the controller begins monitoring the new transducer offset voltage. If the offset voltage is not between the limits after an 8 sec delay and then an 8 sec test period, a standard alarm sequence is started and the LUBE OFFSET ERROR message displayed. When the faulty transducer is disconnected and replaced with new one, the controller monitors offset voltage for another 8 consecutive one second intervals. This cycle is repeated until a lube transducer offset is determined to be within range. The alarm clears if the offset voltage is within range for the 8 second period. When an acceptable offset has been identified, the controller then uses the offset value until the transducer is removed. This alarm cannot occur if the lube transducer is removed.

When a lube transducer is disconnected or not properly inserted a standard alarm sequence is started and the LUBE XDUCER REMOVED message displayed. The alarm clears when a lube transducer is properly connected. No lube related alarms, except LUBE VOLUME LOW and LUBE XDUCER REMOVED, can occur when a transducer disconnect is verified. The alarm can occur before, during or after the pump has been started but not before a transducer has been inserted at least once.

The time period ($\Delta T$) between consecutive zero crossings of dP/dt is monitored. If $\Delta T$ is outside the range for 6 consecutive zero crossings then a standard alarm sequence is started and the LUBE PHASE SHIFT message is displayed. If the alarm condition is observed not to occur for a continuous time period of 1 second then the alarm clears.

This alarm cannot occur when the lube transducer is disconnected. The alarm is not be issued it the pump is stopped.

The lube line is monitored for the presence of air at one second intervals. If a bubble of sufficient volume passes the bubble detector transducer then a standard alarm sequence is started and the LUBE LINE OPEN message is displayed.

The alarm is mutable. The alarm is latched and only cleared if the mute button has been pressed while the message appears on the alarm list and no air is detected in the lube line.

As a secondary indication, the yellow LED is illuminated during a LUBE LINE OPEN alarm.

The blood pump 316 is controlled by the controller 332, as shown in FIG. 11. Therefore, the flow rate through the blood pump 316 can be adjusted by the technician. This is accomplished in the blood pump 316 by changing speed of the impeller 334. A technician adjusts the controller 332 for attaining a desired impeller speed based on the arterial pressure of the patient and the flow rate of blood through the blood pump 316. Generally, it is desired to maintain a flow rate of blood of between 1.0 and 3.5 liters per minute through the blood pump, and an arterial pressure of 60–70 mm of mercury in the patient. The arterial pressure of the patient can be obtained from standard techniques of obtaining blood pressure.

The flow rate of the blood through the blood pump 316 can be identified by measuring the impeller speed and stator current, as described in U.S. patent application Ser. No. 09/130,617 (PCT application PCT/US99/17465), incorporated by reference herein. The flow rate is displayed on the controller, where the technician uses the information to change the impeller speed. The impeller speed is maintained between 3000 and 7500 rpm. If the estimated flow is below a preset low flow alarm limit, a low flow alarm is activated to warn the technician of potentially unsafe conditions, such as impeller speed too low or too high and cannula kinking or distortion. Impeller under speed can cause regurgitant flow from patient's artery, through the pump, and into the heart and thus impair patient's heart function. Excessive impeller speed can cause patient's heart collapse and introduce heart damage. Cannula kinking can cause blood clotting in the cannula and lead to pump failure. Cannula distortion may cause patient's organ under perfusion.

The low flow alarm also provides prevention of removing gases from the circulated blood stream into patient's body due to an excessive vacuum pressure created at the pump inlet.

Since the controller is able to detect low flow conditions, which might be due to unsafe operation of the system, this would provide an easier way for patient care and a better safety feature to patients.

When the patient is stationary, and thus the controller is stationary, the controller and the blood pump are powered from the AC mains available through the walls of the room. The controller also has a battery operation, which is used for patient transfers, and more particularly from the catheter lab to the ICU or operating room.

Figure 16A:
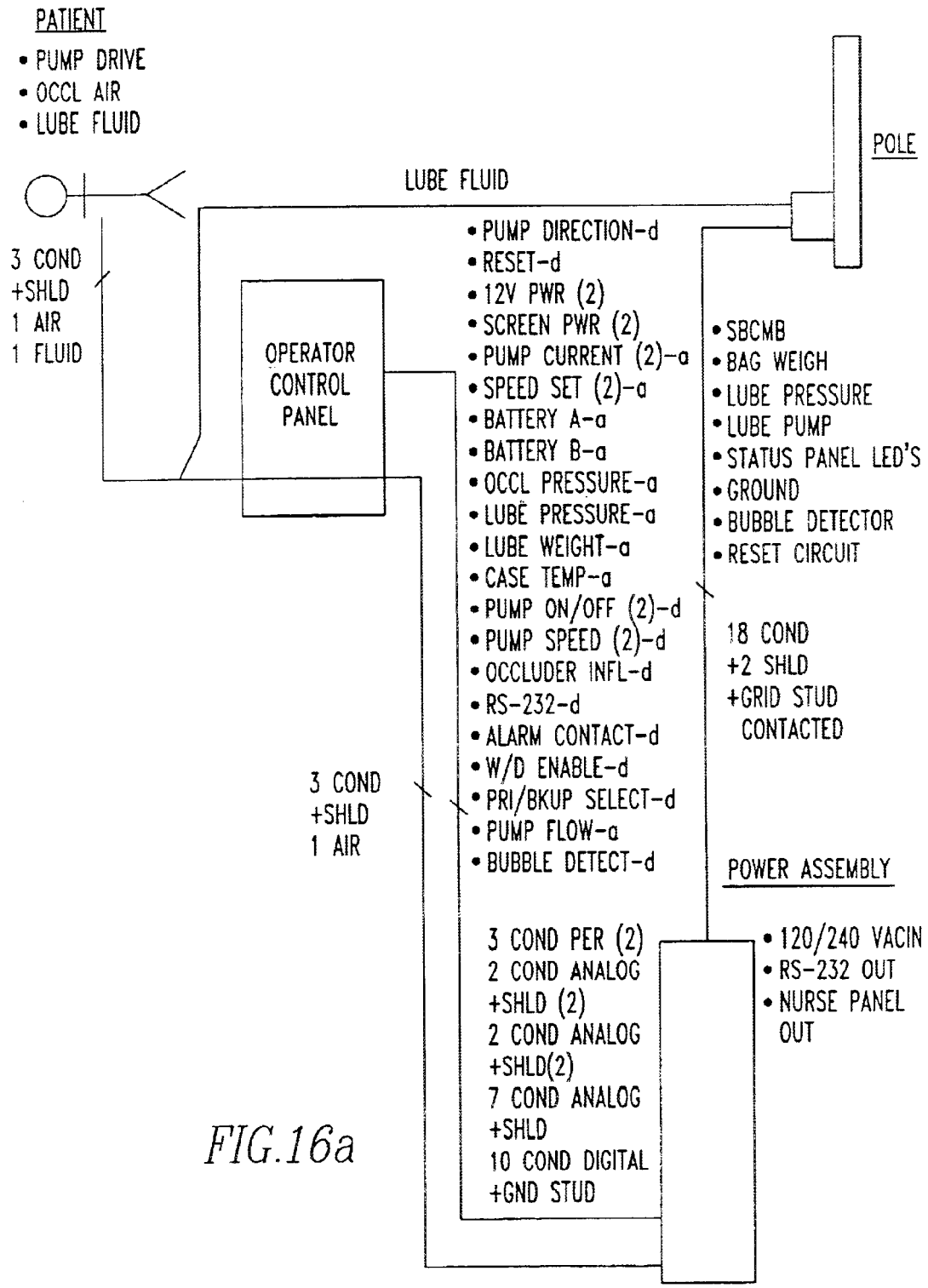
FIGS. 16a–16e are schematic representations of the blood pump controller.
Figure 16B:
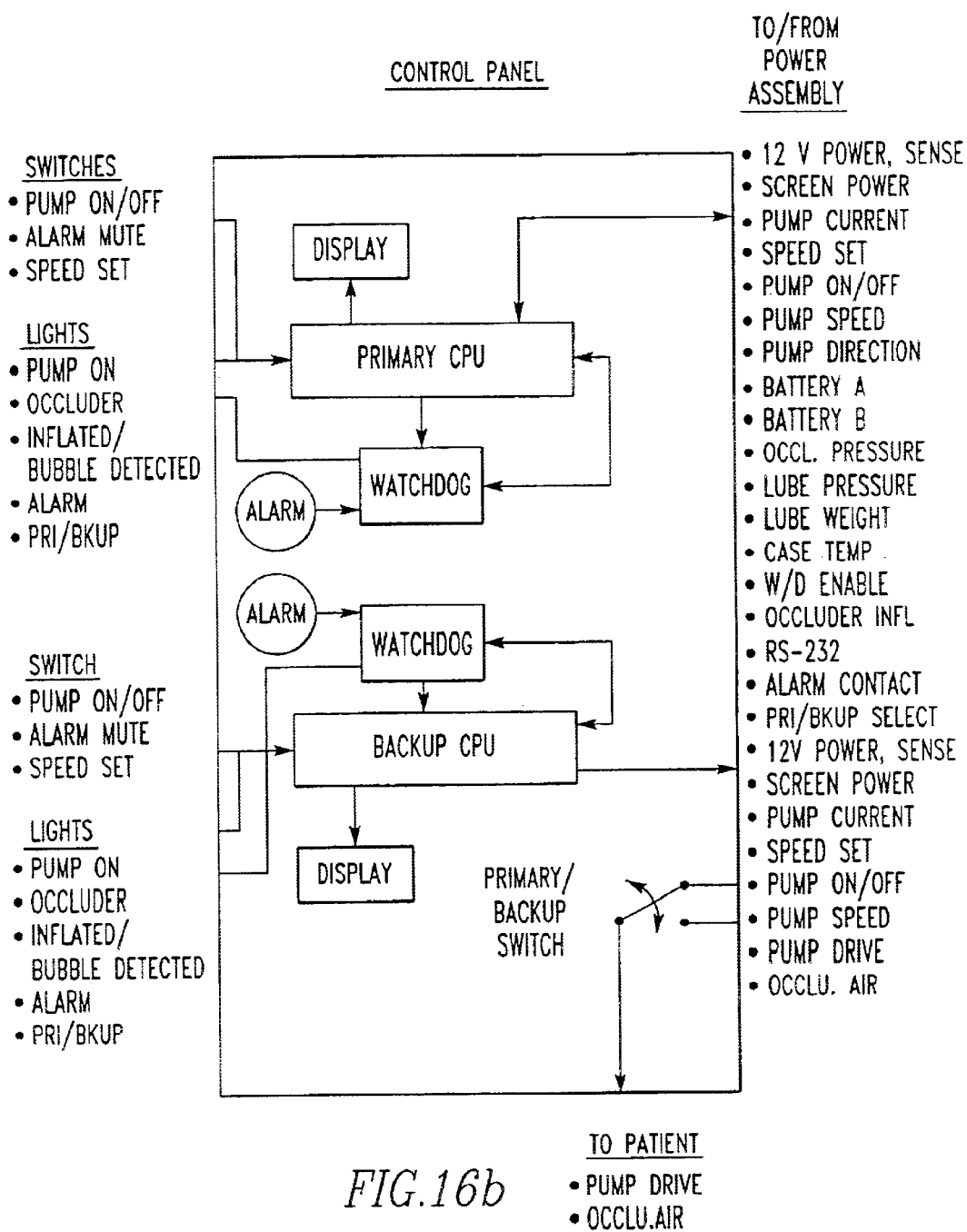
Figure 16C:
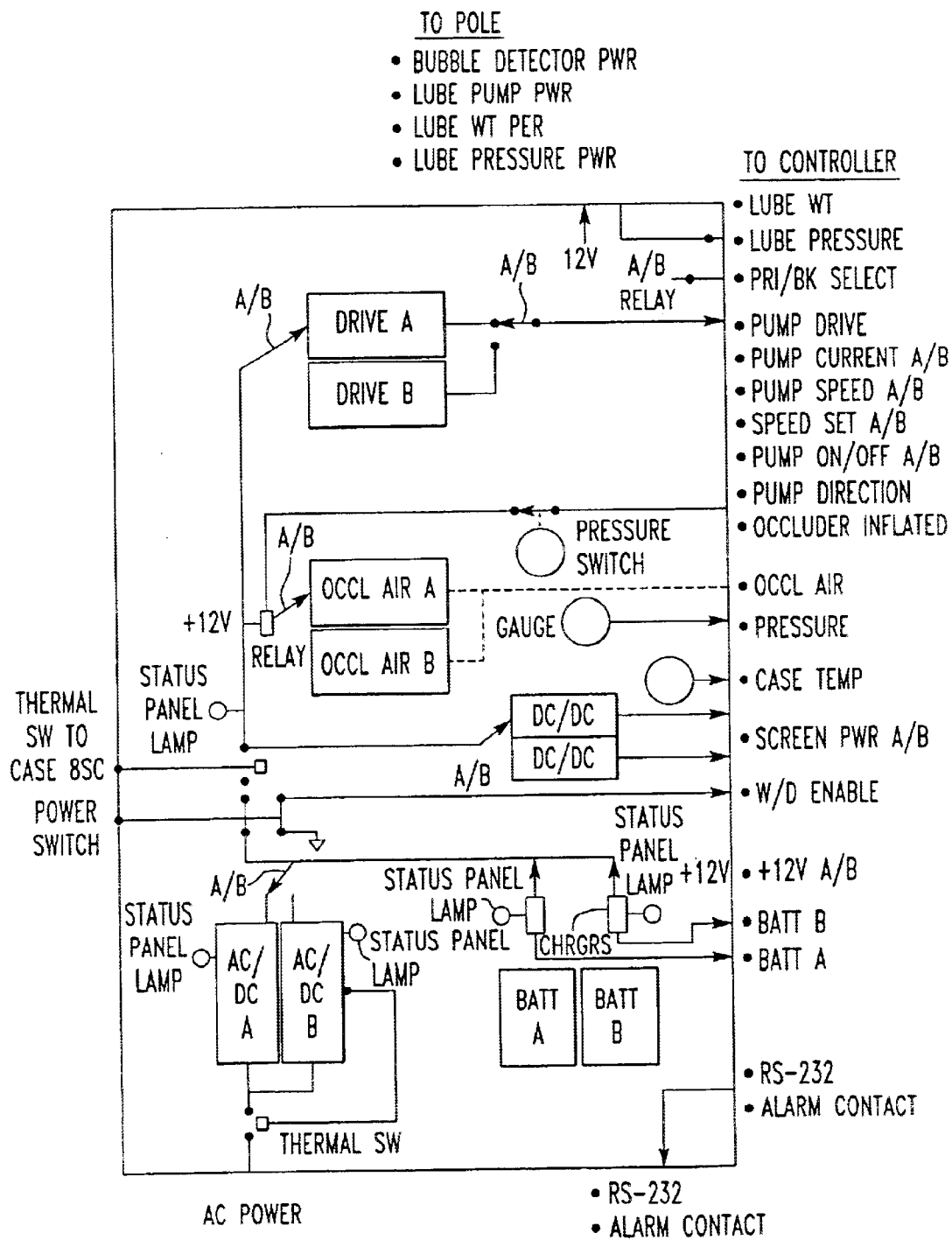
Figure 16D:
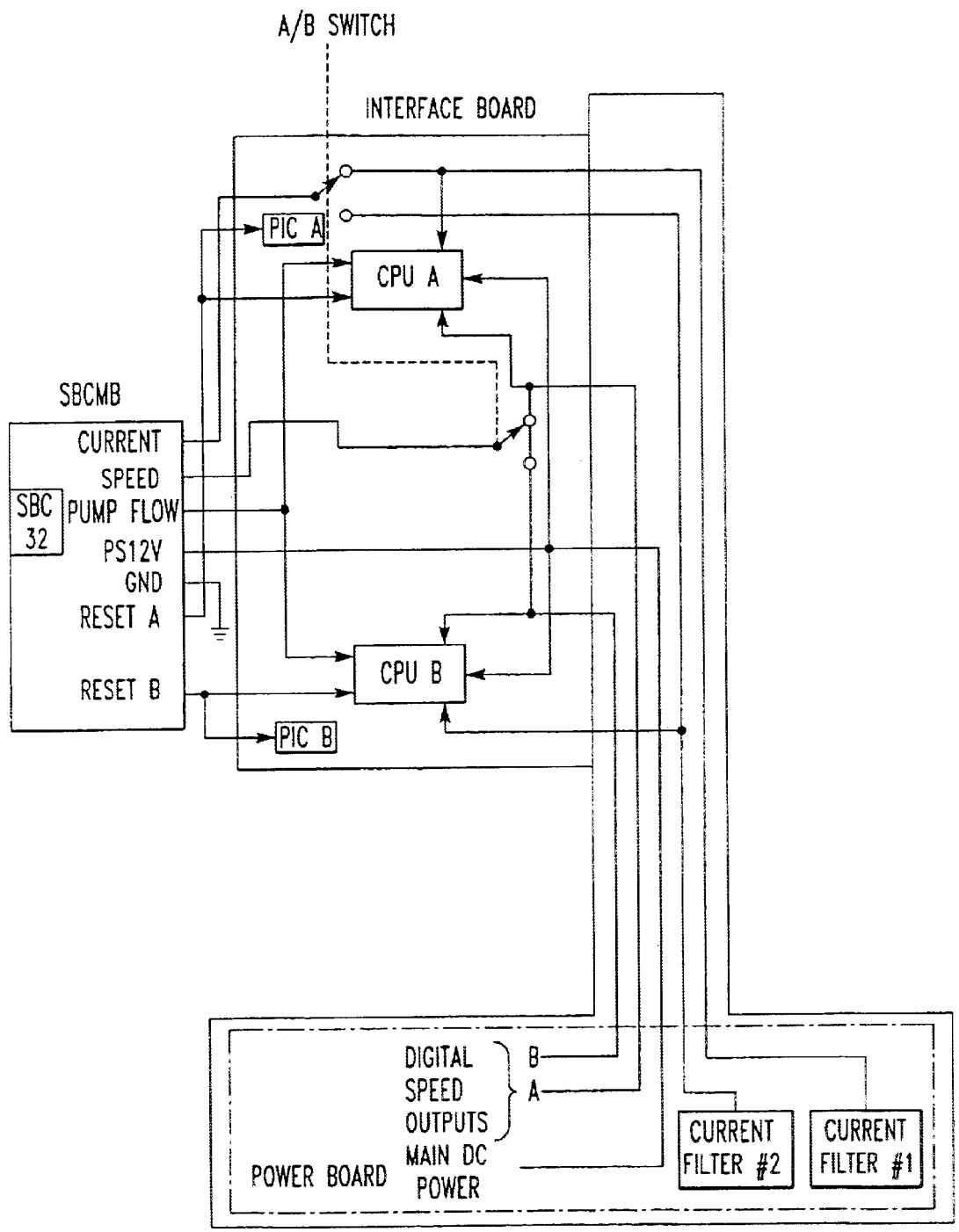
Figure 16E:
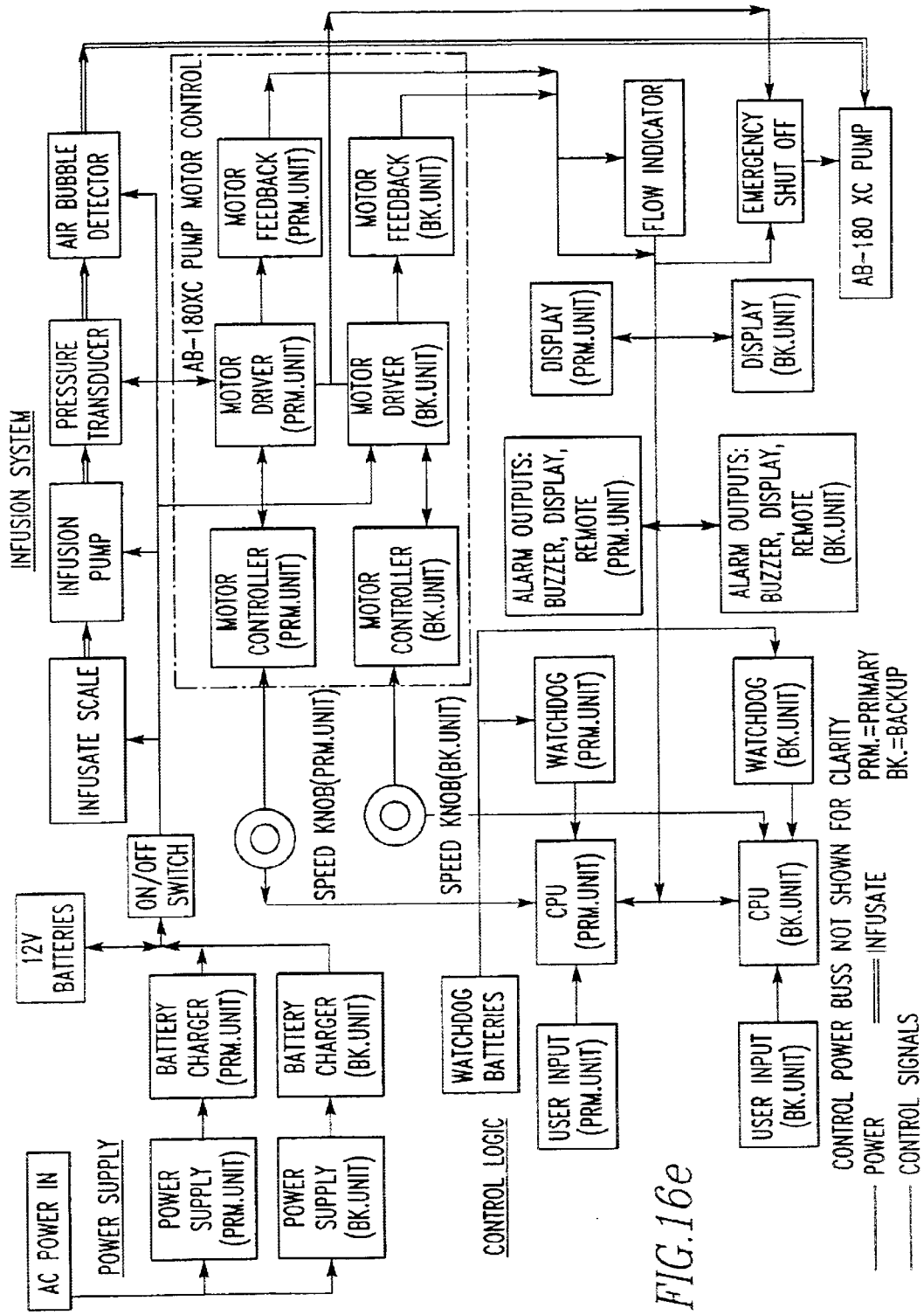

The power supply system provides power to the pump. The power supply system consists of a switching power supply, a battery charging supply, and the necessary control circuitry, as shown in FIGS. 16c–16e.

The switching power supply provides power to the controller when the controller is connected to AC power (with power switch on or off). The battery provides a minimum of 30 minutes of operation under maximum load conditions.

A warning is generated in the controller when switching to battery operation to tell the user the system is operating on battery power. A low battery alarm is generated, which cannot be muted, when the battery output is less than specification giving the user warning of 10 minutes remaining on battery operation. When the battery voltage has decayed to the battery depleted threshold, new alarm messages are displayed (PUMP AUTO OFF; RECONNECT AC PWR), the pump is shut off. The ALARM/MUTE switch will not silence this alarm. This alarm can only be silenced by connection to AC power.

The system is designed for a single mode of operation. All setup and service operations are done from the normal operating mode.

The control system is divided into three distinct parts: an operator control panel, a support stand and a power assembly. The system is shown in FIGS. 16*a*–16*e*.

The operator control panel is an electronic control system that includes the system computer, status display and operator controls. It is attached at about shoulder height to the support stand to provide optimum display readability and easy hand access to the operator controls. The height of the control panel can be adjusted. The operator panel has dual control units, a primary unit and a backup unit. The dual unit design provides dual integral displays and dual computers for redundant operation. A hinged door is used to cover the display panel not being used (normally the backup display). A knob is provided to manually switch control to the backup unit as described below. The door can be moved to cover the primary display and is mechanically interlocked with the "primary—backup" control knob to eliminate inadvertently covering the active controller.

The support stand is a vertical post with a square pedestal base with castors. It provides an attachment point for the control panel, power assembly and lubricating fluid components. It also contains the wires which interconnect the system components and the height adjustment subsystem.

The power assembly is located at the base of the support stand and contains the power system, the battery and implant pump drive electronics. The system power switch is located here.

The control system architecture provides for fault tolerance while minimizing the failure rate of the system controlling pump operation. As shown in FIG. 16*e*, the user can only turn the pump on or off and change the speed between minimum and maximum speeds. Speed control is performed by hardware, with the user input determining voltage from a potentiometer that is then fed directly to a motor control/drive circuit, which then feeds current directly to the motor. All other control functions provide only monitoring of the system parameters, which are performed in parallel with the motor and pump operation. Should a monitor function fail, the system will maintain pump operation but will alert the user to the failure of the monitor system. The user can then switch to a backup control system to again begin effective pump monitoring. In other words, the monitoring is not directly involved with motor operation, in which case any monitor failure might affect patient treatment.

Pump speed is controlled by the selected (primary or backup) potentiometer (speed pot) on the control panel which is wired directly to the motor control chip. The motor control chip independently starts the motor and controls the speed in accordance with the speed potentiometer setting. The CPU monitors the speed pot voltage and compares it to the actual pump speed determined by the voltage-controlled oscillator (VCO) frequency to confirm that they are within the specified tolerance. The CPU monitors pump direction via a direction detection circuit located on the power board. If the CPU detects pump direction reversal, it provides an appropriate type 2 alarm.

The control system is designed with redundancy for all subsystems (except for the lubricant infusion subsystem). The redundancy is structured as two parallel control units with the exception of the battery, which is structured with independent redundancy. Under normal operation, both computers are operational but only one is in control, recording data and generating alarms based on the setting of the primary/backup knob. A circuit is included to alarm a dual control unit failure. The primary and backup computers are separate without exchanging information.

The control panel is divided into two halves: 1 primary system and 1 backup system. Under normal operation, the blood pump is controlled using the primary control unit. If a runtime failure occurs in the primary control unit, control can be manually switched to the backup control unit. Circuitry is also provided to monitor the backup computer.

Because of the requirement to always have two operational control units available before implanting the cardiac pump, when power is turned on, both primary and backup control units perform a startup self test sequence. If either computer is not functional, an alarm condition is evident. If the primary computer does not function the primary light on the primary/backup select knob indicates the failure, the backup light flashes green and a non-mutable audible alarm is sounded. A PRIMARY CPU FAIL message appears on the backup controller. If the backup computer does not run, a BACKUP CPU FAIL alarm is posted on the primary control panel and the backup light on the primary-backup select knob indicates the failure. A mutable audible alarm occurs. If the proper functioning of components in the system other than the computers must be verified, they should be checked by the operator.

Both primary and backup systems must be fully operational for the control system to be used. If a startup failure is detected in either the primary or backup control unit, the entire control system should be rejected. If the BACKUP CPU FAIL appears on the display, at any time, then the controller should be replaced since backup patient support is unavailable.

The system power and pneumatic components are located in the power assembly. If a failure of any power or pneumatic component occurs, the backup component set can be selected by manually switching the control unit on the control panel. The two redundant batteries are always connected and use semiconductor and mechanical fusing to automatically disconnect a failed battery.

If a primary to backup switchover is performed while the pump is running, the pump shuts down. If a primary to backup switchover is performed while the pump is stopped, the pump remains stopped.

All switches are labeled and recessed or guarded to prevent inadvertent operation. All controls occur in duplicate except the primary/backup select knob and the power switch.

A recessed rotary knob is supplied to control pump speed. The knob does not have any quantitative markings but is labeled Pump RPM and "◄■" to indicate that turning the knob clockwise increases speed (hence flow rate). When the pump is started, it comes to a speed determined by the angular position of the knob. The speed can then be increased or decreased by rotating the knob. The actual pump speed is determined by observing the RPM readout on the display which is measured directly from the pump drive electronics.

When an alarm condition occurs, a flashing RED light occurs, the audible alarm is activated and an alarm message is displayed.

A rotary knob is built into the control panel which selects the operable system components. It is labeled "Primary" and "Backup" and has a circular indent to point to the selected subsystem.

The display screen is touch sensitive and has three main buttons: SERVICE DATA, CONFIG MENU and WEAN MENU. The CPU activates an audible chirp when it senses a touchscreen button press.

The SERVICE DATA is used to display system parameters not needed for normal pump operation. Pressing the SERVICE DATA button again exits the system parameter display.

The CONFIG MENU button is displayed when the SERVICE DATA button is pressed after power on but before the pump is started (this prevents CPU controller reset while the pump is running). The configuration menu is a user interface that consists of clearly labeled and intuitive touchscreen buttons for adjusting the controller time, RS-232 port setting, date, and language. The settings are stored in non-volatile memory and are recalled when the controller is powered up. The CPU maintains the time/date and the CPU EEPROM holds the latest language and RS-232 configuration setting. The selectable languages are English, Spanish, German, Italian and French. The selectable RS-232 port settings are direct (to PC) or modem.

The WEAN MENU button only appears while the pump is running or after the pump has been stopped. The WEAN MENU button replaces the CONFIG MENU button if the pump is started when the service data is being displayed. The WEAN MENU allows the operator to temporarily disable the PUMP FLOW LOW alarm during patient weaning.

System power is directly controlled by a guarded, manual switch. If the system is off, pressing the power button supplies power to the controller. Selection of primary or backup power is controlled by the primary/backup knob on the control panel as described above, however, selection of primary or backup battery is automatic. Status of system power is displayed by visible LED indicators.

If the system is on and the power button is pressed, system power is removed and the controller stops. Any audible alarms are silenced. Battery charging continues as long as AC power is supplied.

All parameters and messages are displayed on a backlit monochromatic graphics display with alpha numeric capability and a touch-sensitive overlay. The messages are grouped into three sections: Normal operating parameters, alarms and system parameters.

During normal operation, with the pump on and no alarms, several messages are presented on the display. These include: SYSTEM READY, SERVICE DATA, WEAN MENU, XXXX rpm and Y.YY lpm where XXXX is the pump speed and Y.YY is the pump flow rate. If the pump is stopped, XXXX RPM and Y.YY LPM are replaced by the message PUMP OFF HH:MM:SS.

If an out of range reading is observed for any of the monitored system parameters, the audible alarm is sounded and the red alarm light is illuminated. Appropriate alarm messages are displayed.

An audible alarm is provided to indicate that a new alarm condition has occurred. The alarm can be silenced by pushing a mute button except under certain conditions.

A number of indicator lights are provided to tell the operator the status of the pump, the occluder, alarms, system power, and bubble detector status.

The controller has external connections for the implant pump, system power and external data communications.

The controller is designed so that initial set-up and testing can be performed by a single non-sterile operator.

The pump is started by pushing the PUMP START/STOP button while the pump is in the OFF state.

The pump is stopped by pushing and holding the Pump Start/Stop button for 5 seconds while the pump is in the ON state. The typical pump stop sequence would be as follows:

Press PUMP START/STOP button.

The controller initiates the pump stop sequence by displaying the HOLD BUTTON X message (a short beep is issued).

The HOLD BUTTON X message where X=the seconds remaining until the pump shuts down is the controller's confirmation to the operator that the button is being pushed.

After 5 seconds, the pump is turned off.

The PUMP START/STOP light will switches green to off.

The PUMP OFF HH:MM:SS message is displayed and starts counting. The PUMP STOPPED alarm is posted.

If any of the alarm conditions that require shutting off the pump occurs, the pump is shut down and the PUMP STOPPED alarm message is displayed. When the pump stops, either from an operator command or an alarm condition, a "PUMP OFF" timer is started and the elapsed time since pump stop is shown on the display with the message PUMP OFF HH:MM:SS. If an primary to backup switchover is performed while the pump is running the pump shuts down and the messages PUMP STOPPED and PUMP OFF HH:MM:SS are displayed on the backup display.

If a primary to backup switchover is performed when the pump is off then the pump will remain off and the messages PUMP STOPPED and PUMP OFF HH:MM:SS will be displayed on the backup display.

If the pump is restarted and runs for at least 1 second, the PUMP OFF timer is reset to zero.

Stator current is monitored at 1 second intervals. An alarm condition is established and latched if the running average of any 5 consecutive measurements is out of specification.

If an alarm condition is detected, a standard alarm sequence is started and the PUMP CURRENT HIGH message displayed.

Pump speed is monitored at 1 second intervals. An alarm condition is established if 3 successive speed readings are out of specification. If the alarm condition occurs, the pump will be stopped.

Pump current is checked first. If the current for any of the previous 3 readings was below the low current limit, the alarm shall be handled as a pump current low failure. If all 3 previous readings were above the low current limit, the alarm is handled as a high speed failure.

If the alarm is to be handled as a pump speed high alarm, the pump will be stopped. A standard alarm sequence shall be started and the PUMP SPEED HIGH message displayed.

It is normal to transport the patient from the operating room to a recovery room with the system attached to the patient and operating. This requires removal of AC power. The control system is designed for a minimum of 30 minutes of battery operation.

If the voltages on batteries A and B drop below the threshold and the AC power is disconnected, a system power failure alarm condition is established within 1 second. The pump is stopped, a standard alarm sequence is started and the BATTERY DEPLETED message displayed.

The audible alarm cannot be muted. The alarm clears when the AC power is restored.

System power (DC at the power supply) is monitored at 1 second intervals. If 3 consecutive AC Power Lost conditions are observed, a standard alarm sequence is started. An AC POWER LOST message is displayed. If the AC power restored condition is established for 3 consecutive 1 second intervals, the message will clear. The AC power status is also echoed by the status panel indicators.

If battery A or battery B voltage drops below the battery fail voltage threshold for 1 second, but both batteries are not below the battery fail voltage threshold, a standard alarm sequence is started. The BATTERY BACKUP FAIL message is displayed. If both batteries exceed the BATTERY BACKUP FAIL voltage threshold for 1 second, the BATTERY BACKUP FAIL alarm will clear.

If both the A and B battery voltages drop below battery depleted voltage threshold for 1 second, but the system DC voltage is normal, i.e., AC power connected, a standard alarm sequence is started. The BATTERY DEPLETED message is displayed. If the DC system voltage is normal and at least one battery reaches the battery depleted voltage threshold, for 1 second, the BATTERY DEPLETED alarm will clear.

If either the C or D watchdog (WD) battery voltages drop below the WD battery low voltage limit or rises above the WD battery high voltage limit for 3 seconds, a standard alarm sequence is started. The WD BATTERY FAIL message is displayed. If both C and D battery voltages rise above a threshold but less than WD battery high voltage limit for 1 second, the alarm will clear. A watchdog battery is considered depleted below the WD battery low voltage limit and is considered removed from the circuit if the voltage is greater than the WD battery high voltage limit.

If, for 3 consecutive 1 second readings, the voltage on both batteries drops below the battery low voltage threshold and the system voltage is below the specified limit, a low battery condition is set. A standard alarm sequence is started and the BATTERY LOW message is displayed. The audible alarm cannot be muted while the low battery condition exists. The BATTERY LOW message will clear and the audible alarm will automatically silence if the system DC voltage and the voltage on both batteries exceeds the alarm limit, specified in the alarm table, for 3 consecutive 1 second readings.

If the backup unit fails, a standard alarm sequence is started. The BACKUP CPU FAIL message is displayed. If a primary unit failure occurs while the backup unit is selected then a standard alarm sequence is started and a PRIMARY CPU FAIL message will be displayed. The PRIMARY/BACKUP CPU FAIL alarm can occur at any time when the controller is on. This alarm is non-mutable.

The temperature of the power board case in the region of the primary and backup motor control chips are measured at 1 second intervals. If the temperature exceeds the temperature threshold, a standard alarm sequence is started and a POWER ASSY TEMP HIGH message displayed. The alarm clears if the temperature drops below the alarm limit.

The AB-180 pump is controlled by a dedicated motor control chip which has three nested control loops. For each loop, the parameters must be selected by the designer to give the desired dynamic operation over the full range of pump speeds.

The loop parameter settings for optimum dynamic operation are not consistent with reliable startup performance. Startup can be erratic with chatter and in the worst case the pump refuses to start at all. These symptoms vary with the setting of the speed control knob. Also at higher speed settings there is significant speed overshoot which could be damaging to blood cells. The control circuit parameters for reliable startup at the minimum pump speed were determined, considering the special algorithms in the control chip that operate during startup to limit current and sense rotor position. The parameters for optimum dynamic operation were then determined over the full speed range.

Figure 28:
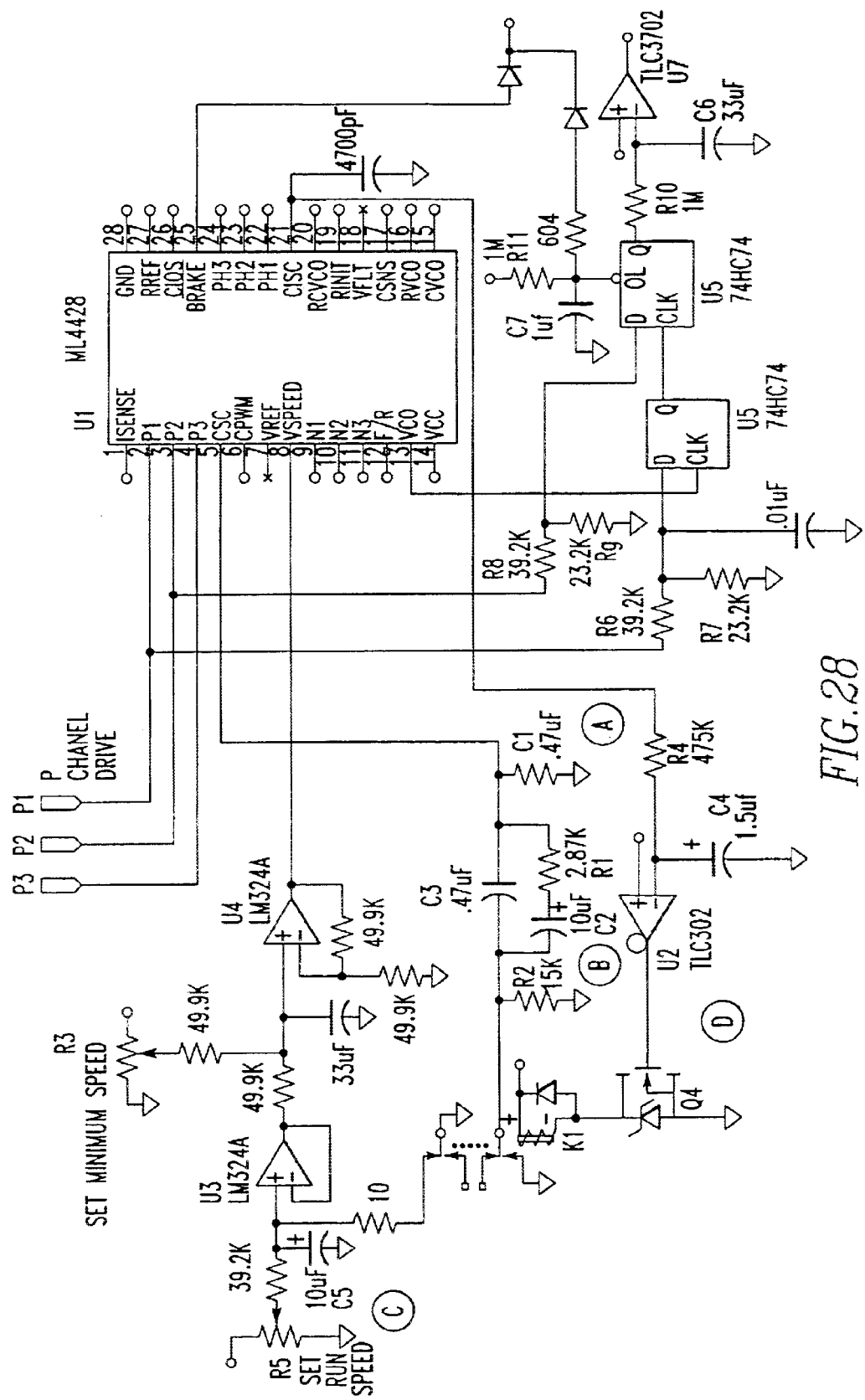
FIG. 28 is a schematic representation of slow start circuitry.
Figure 29:
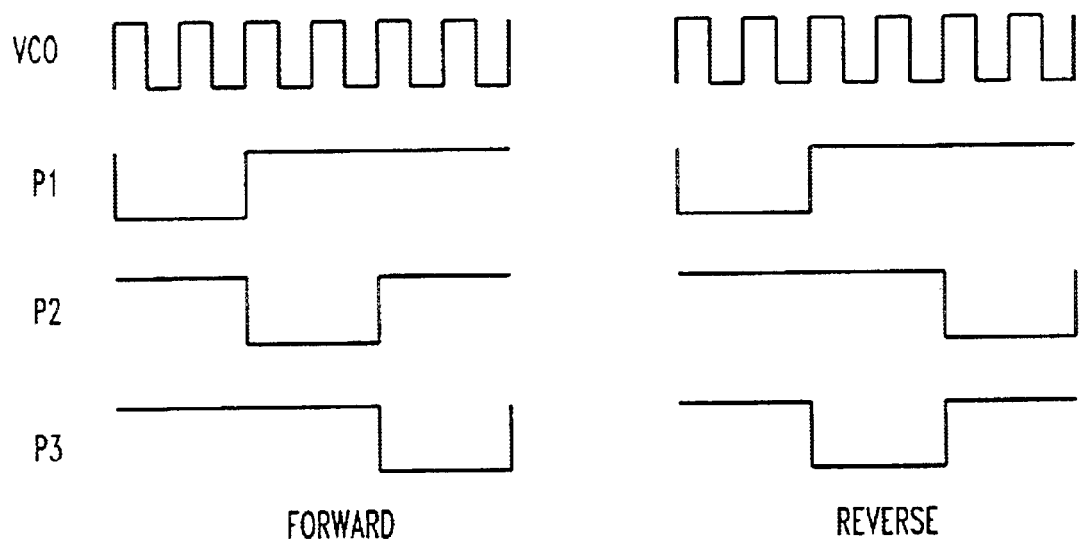
FIG. 29 is a schematic of timing circuitry.

Referring to FIG. 28, the key speed control concept employed to offer stable speed and soft speed change without overshoots involves switching between two different sets of loop filter components, A and B. The point at which switching occurs is determined by the circuitry at D. The switching also changes the speed between upper and lower settings provided by the user. The circuitry at C determines the rate of speed change between the upper and lower speed settings.

The pump speed setting is electronically overridden and held at minimum during the startup sequence, regardless of the setting of the speed control knob. Then the loop parameters are configured for reliable startup and the pump is started. The pump starts and its speed begins to ramp up. When it reaches a predetermined threshold, the loop parameters are automatically reconfigured to their optimum values for dynamic operation and the override of the pump speed setting is released. The pump speed is then allowed to slowly increase to the knob setting.

Pump startup is reliable and smooth since the loop parameters are optimized for startup at one particular speed which is set by the override and startup always occurs at that speed.

Refer to FIG. 28 for a description of this speed modulation control circuitry. U1 is the motor control IC. Only the pertinent connections are shown. The pump speed is proportional to the voltage at the VSPEED input (pin 8). RUN/STOP signal is low when the pump is off and the voltage at CISC (U1, pin 21) is high. This forces comparator U2's output to the low state which holds transistor Q4 off and relay K1 de-energized. In the de-energized position K1 has two effects. The lower contacts of K1 cause the loop filter components connected to U1's CSC line (U1, pin 5) to be set for proper startup. Capacitor C1 is connected from pin 5 directly to ground and components R1, C2, and C3 are connected to ground through resistor R2 which provides isolation and a DC return path. The upper contacts of K1 pull the non-inverting input of op amp U3 to ground. This causes the voltage determined by the minimum speed set potentiometer R3 to appear at U1's VSPEED input.

When the RUN/STOP signal is taken high, U1's BRAKE line (pin 25) is released and the pump is started. Its speed begins to ramp up to the minimum speed setting. As U1's control loops settle to their locked condition, the voltage at CISC (pin 21) begins to drop. This CISC voltage is filtered and delayed by the R4/C4 network and its drop is sensed by comparator U2. U2 then turns on Q4 which energizes relay K1. U2 incorporates hysteresis which is not shown in the figure and is a high input impedance device to avoid loading the CISC signal. When K1 is energized, its lower contacts connect C2 and C3 directly to ground which sets the loop filter components to the desired configuration for normal pump operation. K1's upper contacts release U3's non-inverting input and capacitor C5 begins to slowly charge to the voltage set by the run speed potentiometer R5. Op amps U3 and U4 then cause the voltage at U1's VSPEED input to be determined by the run speed setting.

It can be appreciated from the above description that the speed modulation circuitry provides a convenient means of ramping the pump speed between two user selected settings in a controlled manner. This technique would allow the pump output to be varied in a pulsatile manner using only a simple digital signal for control. The control signal could be provided by a simple oscillator which could have an unequal duty cycle. The time constants of the ramp rates can be adjusted as desired by proper component selection or minor changes to the circuitry of FIG. 28. Note that other more complex means could also be used to implement a pulsatile flow control. Pulsatile control with this circuit concept could be implemented in software.

It is possible to simulate the varying blood pressure of the normal heartbeat by modulating the speed of the pump to obtain pulsatile flow.

The actual pump speed is compared to the speed potentiometer setting at one second intervals. If a deviation greater than that specified is detected, for 6 consecutive intervals, then a standard alarm sequence is initiated and the PUMP SPEED ERROR message is displayed. The alarm clears if the deviation is less than the limit specified in the alarm table for one second.

The actual pump speed is monitored by the CPU after the CPU sends the pump shutdown signal. If the actual pump speed is greater than the alarm threshold specified then a standard alarm sequence is initiated and the PUMP SHUTDOWN ERROR alarm is displayed. The alarm clears if the pump is restarted. The alarm clears if the pump speed decreases below the alarm threshold when the CPU has established a pump off condition.

The pump flow estimate is monitored at one second intervals. If a blood flow rate less than the limit specified is detected then a standard alarm sequence is initiated and the PUMP FLOW LOW message is displayed. The alarm clears if the flow rate rises above the limit specified in the alarm table. This alarm can only be disabled via the WEAN MENU. The alarm defaults to enabled at controller power up. The alarm automatically re-enables within a specified period of being disabled.

Another safety feature of the system is its ability to detect if the motor controller is improperly causing the pump to spin in the reverse direction. The control IC has the ability to spin the pump in either direction. Unintended reverse operation is a concern to regulatory agencies regardless of its low likelihood of occurrence.

Pump direction is monitored via a direction detection circuit located on the power board. The circuit outputs logic high for forward direction and logic low for reverse. The direction detection circuit is monitored at one second intervals. If pump reversal is detected then a standard alarm sequence is initiated and the PUMP DIRECTION ERROR message will be displayed. The alarm can occur with the pump on or off. When the pump is on the PUMP DIRECTION ERROR alarm clears if the pump reverses direction. A PUMP DIRECTION ERROR alarm when the pump is off suggests a direction detection circuit failure and the alarm can only be cleared if the fault is repaired by service personnel.

Referring again to FIG. 28, U1 signals P1, P2, and P3 (pins 2, 3, and 4) are the drive lines to the P channel FETS in a standard three phase bridge motor driver. These signals are logic outputs which are driven in a specific sequence as the three phases of the motor are energized. When the pump is spinning in the forward direction the sequence is P1, P2, P3 and in reverse it is P1, P3, P2. The pulses are low for two cycles of the VCO clock output (pin 13) and transitions occur on the positive going VCO clock edge. Note that the N channel outputs (pins 9, 10, and 11) are not suitable because in an analog control scheme they vary in amplitude and in a pulse width modulated scheme they are high frequency pulses that bear no relationship to the phase sequence.

The direction of pump drive is determined by examining the P line sequence using digital logic. FIG. 28 is a timing diagram which shows both the foreword and reverse sequences. To determine direction, the P2 phase is sampled shortly after the high going edge of the P1 phase. If the sample is low, the direction is foreword. If the sample is high, the direction is reverse. It will be appreciated that any phase could be used for the reference and either of the remaining phases could be sampled. Also it is possible to sample both of the remaining phases.

D type flip flop U5 is used to delay the P1 signal by one VCO clock period. The rising edge of the delayed P1 signal then clocks D type flip flop U6 to sample the P2 signal. The sampled P2 signal appears at the Q output of U6. It is filtered by the R10/C6 network and applied to comparator U7 which produces the DIRECTION output. Comparator U7 also incorporates hysteresis which is not shown. Resistors R6, R7, R8, and R9 reduce the voltage of the P1 and P2 signals to the logic level required by U5 and U6. The R11/C7 network holds the direction output at foreword until the control loops have stabilized.

A runtime random access memory (RAM) test is implemented by periodically checking critical values against duplicate inverted values. If any of the critical variables cannot be verified then a standard alarm sequence is started and the RAM TEST FAILURE message is displayed. The alarm clears if all critical variables can be verified in a subsequent cycle of the runtime RAM test.

A runtime read only memory (ROM) test checks the application code space in Flash memory. This test is completed approximately every 5 minutes or less. If the test is not completed successfully then a standard alarm sequence is started and the message ROM TEST FAILURE is displayed. The alarm clears if a subsequent ROM test passes.

The CPU supply voltage is monitored in 1 second intervals. If the CPU supply voltage exceeds the alarm limit then a standard alarm sequence occurs and the message CPU VOLTAGE HIGH is displayed. The alarm clears if the CPU voltage decreases below the specified alarm limit for one interval.

The CPU supply voltage is monitored in 1 second intervals. If the CPU supply voltage drops below the alarm limit then a standard alarm sequence occurs and the message CPU VOLTAGE LOW is displayed. The alarm clears if the CPU voltage increases above the specified alarm limit for one interval.

A runtime CPU self test is completed approximately every 10 seconds or less. If the test is not completed successfully then a standard alarm sequence is started and the message CPU TEST FAILURE is displayed. The alarm clears if a subsequent CPU self test passes.

The WD (PIC) toggles a signal to the CPU when the WD sends its strobe. When the CPU fails to detect the holdoff signal from the PIC within 1 second then a standard alarm sequence is started and the message PIC FAILURE is displayed. The alarm clears if the WD resumes sending CPU holdoff signals in less than 1 second intervals. In addition, the WD also monitors the CPU communications to confirm CPU status.

The CPU initiates an air bubble detector self test approximately once every 1 minute. If, during the self test, the air in line response is not confirmed by the CPU within 1 second then a standard alarm sequence is started and the message AIR DETECTOR FAILURE is displayed. The alarm clears if a subsequent air detector self test passes.

When the controller passes its internal startup self tests successfully, the CPU displays the SYSTEM READY message. The SYSTEM READY message remains posted while the computers are functioning normally as established by the runtime self tests. The only exceptions are that the SYSTEM READY message is not displayed when the configuration menu is displayed and SYSTEM READY is not displayed when BATTERY ON XXX MIN is displayed.

The pump can only be started when SYSTEM READY appears in the display.

Hardware watchdogs are provided for both the primary and backup control units. If the control unit selected by the primary/backup selector knob fails to start or fails during operation, the watchdog circuit alarms. The alarm is a type 2 mutable. The primary/backup switch LEDs indicate system status.

Pump power is controlled by removing motor power from the motor drive and pulling the brake pin of the motor control chip low. Removing power from the drive circuit is needed to assure that current to the motor can be removed even if drive transistors short. When the CPU sends the signal to shutdown the pump it continues to monitor the VCO frequency to verify that the pump stopped.

To turn the pump on, the CPU will send a voltage level command to the power board. This controls a relay that applies power to the pump drive chip and releases the brake line.

Pump speed is measured by counting VCO pulses from the motor drive chip. The drive chip produces 12 pulses per revolution of the motor, so RPM=pulse rate per sec×60 sec per min/12 pulses per revolution=Pulse rate (Hz)×5.

Figure 24:
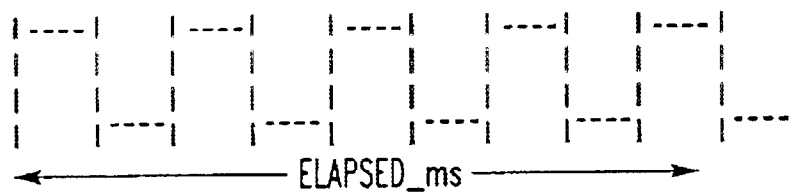
FIG. 24 is an illustration of how the ML4428 pulse train is processed.

FIG. 24 serves as an illustration of how the motor control chip pulse train is processed.

Pump flow is derived using Non-Invasive Flow Estimation Algorithm. See PCT application PCT/US99/17465, incorporated by reference herein. The algorithm samples two analog voltages (16 bit, 200 Hz) that are proportional to pump current and pump speed to compute flow to within ±10% of full scale. The algorithm is derived based on the force balance between the electric torque generated by the motor and the load torque, including the mechanical losses. The flow estimator equation is given by $$\hat{Q} = \left(1.5K^*I - J\frac{d\omega}{dt} - B\omega\right) / (f(\omega))$$

where $\hat{Q}$ is the estimated pump flow rate, $\omega$ is the sampled pump angular velocity, $f(\omega)$ is an empirically determined function of speed, $K^*$ is the product of the number of rotor poles and the motor torque constant, J is the rotor's inertia, B is the viscous friction coefficient, and I is the sampled pump current.

The controller continuously logs system parameters and events on an event driven basis. The log includes a System Parameter Record and an Event List. The entire log is sent to the serial port every 15 seconds. The serial port is configurable for modem or direct PC connection. The maximum data rate is 19.2 kbps.

The System Parameter Record contains the following entries: current time & date; last system power-up time & date; total elapsed run time for the CPU since power-up; pump speed when pump on; pump flow when pump on and the current Service Data Items.

The Event List contains each occurrence of an operator button press, each occurrence or clearing of an alarm and each occurrence of a primary/backup switchover.

If the log takes longer than 15 seconds to send then the next transmission is delayed until the log has completed. This is to ensure that when connecting to the modem or serial port the authorized service technician receives a complete list of the most recent parameters and events.

The current date and time are determined from the real time clock supplied with the CPU board. The clock is settable by the user via the CONFIG MENU button on the touchscreen.

Paged RAM, other than common RAM is available on the QED4 board, address 0–7FFF in Pages 1, 2, and 3. This RAM is used for the log message queue. The runtime RAM test performs a non-destructive read/write memory test on this RAM. A test is implemented by periodically checking critical values against duplicate inverted values. This test is completed every 10 seconds. The critical values to be verified, based on the risk analysis, are pump_state, occluder_state, pump_speed, pump_flow, avg_pump_current, pump_current and battery_voltage.

A runtime ROM test implements a Fletcher's checksum to test the application code space in flash memory.

All available flash memory, including the system code is included in the startup CRC (cyclic redundancy check) test. A 16 bit CRC is computed. The message ROM TEST is displayed during the test.

An EEPROM startup test performs a 16 bit checksum on the EEPROM memory and compares it with the expected checksum stored in a non-volatile EEPROM memory location. The message EEPROM TEST is displayed during the test.

A CPU startup and runtime self test performs a test of the CPU to verify that the registers, including the accumulators, the index registers, and the flags operate correctly. Integer and floating point arithmetic and shifting instructions are also tested. The message CPU TEST is displayed during the startup test only.

A startup display test activates all pixels on the display screen and subsequently clears all of the pixels. The operator must visually verify that all pixels are activated and then cleared to confirm proper display functionality. No messages are associated with this test.

A startup and runtime air detector test are implemented by toggling the air detector's self test line and confirming that the proper response is received from the air detector's signal line. The message AIR DET. TEST is displayed during the startup self test only.

Common RAM is the page zero memory used by all modules for the storage of local and global variables. This startup test performs a destructive read/write memory test and restarts the QED4 after setting a unique pattern in memory to indicate that the test has been run and that it has passed. The message COMMON RAM is displayed during the test.

A number of human factors considerations have been applied to the system. These include:

Simultaneous display of system data and alarms

Functional grouping of operating parameters, operator messages and alarms on the display Consistent alarm and data nomenclature Positioning of the display for easy viewing with adjustable height Audible alarming Kick space at the base of the unit Closed geometry handles to eliminate entanglement of clothing and equipment The handles sized to fit the full range of nursing personnel An equipment box for storage of manuals, cords and other materials Display lighting adequate for both low and high brightness areas All connections between the implant pump and the controller are made at waist height at the control panel. All connections to remote devices are made from the power assembly located at the base of the stand. Connections critical for safety are provided with strain reliefs and/or locking mechanisms.

The system shall have 2 connections for data output. One RS-232 connector is used to send system data to remote computers; standard DB-9 connector with sockets, base panel mounted and menu configurable for use as modem or direct PC connection. One dry contact relay output is provided for connection to a nursing alarm panel; normally closed, access via base panel mounted ¼" female phone jack. The relay opens, to signal an alarm condition, only when the unit is powered on and a type 1 or type 2 alarm occurs.

The pump is a three phase brushless DC (BLDC) motor. The motor is driven by a Micro Linear Corporation Sensorless Smart-Start™ BLDC Motor Controller Model ML4428. The circuit is configured for linear mode operation to minimize noise and to facilitate flow estimation.

A data dump is made to the external data ports every 15 seconds for authorized service personnel use only. The data stream is write only. No external control of the control system is provided. The signal is sent to 1 serial port—connected at the rear base panel: RS-232, half duplex, optically isolated, using standard DB9 connector. A cover is provided to prevent the operator from accessing the serial port.

A battery load test detects certain failure modes of the system batteries that are currently not identified by either the charging system or the software monitoring. Failures that are detected are:

single shorted cells
  high impedance in a cell

When the load test is activated, a high current is drawn independently from each battery by connecting load resistors across them. This high current simulates the system load during battery operation. The system software monitors the battery voltage during the test. The voltage must remain above a threshold to pass the test. The load test gives an indication of capacity since during testing the battery's internal impedance increases as the capacity decreases.

The system can also be used for treatment of oxygenated blood without surgical procedures, such as radiation or drug or gene insertion. Drug insertion can be accomplished by injecting a specified amount of a specific drug into the system infusion IV bag. Delivery of the drug is then specified by the amount of drug inserted and the constant flow rate of the infusion system. Alternatively, drug insertion can be accomplished by connecting a bag, containing fluid or drug to be professed, to the pump inlet, either with a tube, or a channel if the fluid supply and the pump are in a single housing, and an appropriate size of perfusion cannula to the pump outlet to access a patient's blood stream. The desired perfusion rate can be achieved by adjusting impeller speed of the pump. Radiation treatment can be accomplished by accessing blood flowing through the extracorporeal circuit.

The system can be used for the treatment of hemorrhagic shock, providing circulatory support to treat patients suffering from extreme blood loss. Alternatively, the system can be used for regional blood redistribution when re-circulating blood of a patient is needed. The application would be similar to those already discussed, with the mechanics of setup and operation being identical. Locations for blood access are viable depending on the purposes of treatments. For example, blood access at the pump inflow side could be from subclavian vein, sephalicvein, jugular vein, femoral artery, or axillary artery. On the other hand, blood can be returned to patients through the outflow cannulation at axillary artery, femoral artery, or descending aorta via axillary or femoral artery. Selection of cannulae for different applications depends on the location of blood access and patient's size.

The pump fixation (holster) mechanism as described is to be attached to patient's leg. If other blood access sites are used to provide circulatory support, the pump fixation mechanism could be located at different places of patient's body, such as the arm, torso, or shoulder, near the blood access sites by modifying the bottom shape of the holster.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

| Description | Material | Direct Blood Contact | Duration | Biocompatability Level |
|---|---|---|---|---|
| Upper housing | Polysulfone | Yes | <30 days | Class VI |
| Inflow/Outflow Connector Tube | Silicone | Yes | <30 days | Class VI |
| Silicone Adhesive | Silicone | Yes | <30 days | Class VI |
| Impeller | Polysulfone | Yes | <30 days | Class VI |
| Journal | Polycarbonate | Yes | <30 days | Class VI |
| Seal Coating | Polycarbonate based polyurethane | Yes | <30 days | Class VI |

What is claimed is:

1. A system for assisting flow of blood by a patient's heart comprising:

a transseptal cannula adapted to be inserted percutaneously in the femoral vein and extend through the atrial septum from the right atrium to the left atrium;

an extracorporeal blood pump mechanism having a blood pump for pumping blood received from the left atrium through the transseptal cannula that has been oxygenated, the blood pump inlet connected to the transseptal cannula, the blood pump mechanism includes a transseptal clamp mechanism which clamps the blood pump to the transseptal cannula to avoid undesired disconnection of the blood pump and the transseptal cannula and undesired leaks in a connection joint formed between the blood pump and the transseptal cannula; and a perfusion cannula adapted to be inserted percutaneously in the femoral artery for returning oxygenated blood to the arterial system of the patient, the perfusion cannula connected to the blood pump outlet, and tubing which connects the blood pump to the transseptal cannula and the perfusion cannula, the blood pump connected by the tubing which is within three feet in length of where the transseptal cannula and the perfusion cannula are positioned to enter the patient.

2. A system as described in claim 1 wherein the clamp mechanism clamps the tubing between the blood pump and the transseptal cannula.

3. A system as described in claim 2 wherein the tubing has a continuous smooth inner surface.

4. A system as described in claim 3 wherein the blood pump is a pulsatile, electrical or pneumatic pump having an inflow valve and a perfusion valve.

5. A system as described in claim 3 wherein the blood pump pumps a continuous flow of blood.

6. A system as described in claim 5 wherein the blood pump has a rotor and a stator.

7. A system as described in claim 6 wherein the blood pump mechanism includes a controller connected to the blood pump through which the operation of the blood pump speed is adjusted.

8. A system as described in claim 7 wherein the blood pump includes an impeller which moves against the blood, and the controller adjusts the operation of the blood pump by changing impeller speed.

9. A system as described in claim 8 wherein the controller estimates blood flow rate through the pump only by measuring impeller speed and stator current.

10. A system as described in claim 9 wherein the pump has a hydrodynamic bearing between the rotor and the stator.

11. A system as described in claim 10 wherein the blood pump mechanism includes a fluid reservoir and a fluid pump connected to the fluid reservoir and the blood pump to pump fluid to the blood pump and the hydrodynamic bearing.

12. A system as described in claim 11 wherein the fluid reservoir and the fluid pump connected to the blood pump form an infusion system, and the infusion system is used to monitor for bearing system faults and anticoagulation faults.

13. A system as described in claim 12 wherein the fluid reservoir includes predetermined concentrations of drugs.

14. A system as described in claim 13 wherein the pump controller provides current to the blood pump and the controller includes a battery that provides energy to run the controller and the blood pump, the battery is used for powering the blood pump and controller when the patient is being moved between remote locations.

15. A system as described in claim 14 wherein the blood pump is made of biocompatible materials which have no effect on blood or the patient.

16. A system as described in claim 8 wherein the blood pump mechanism includes an electromagnetic or ultrasonic flow probe in communication with the blood pump and the controller measures flow of blood through the pump with the electromagnetic or ultrasonic flow probe.

17. A system as described in claim 8 wherein the blood pump is a centrifugal pump or an axial pump.

18. A system as described in claim 17 wherein the blood pump mechanism includes a controller connected to the blood pump through which the operation of the blood pump speed is adjusted.

19. A system as described in claim 18 wherein the controller monitors for single point faults, detects and manages them, and alerts users of fault status.

20. A system as described in claim 19 wherein the pump is a pulsatile pump having a stroke time, and the controller adjusts the operation of the blood pump by adjusting stroke time.

21. A system as described in claim 20 wherein the pump controller provides current to the blood pump and the controller includes a battery that provides energy to run the controller and the blood pump, the battery is used for powering the blood pump and the controller when the patient is being moved between remote locations.

22. A system as described in claim 1 including a holding mechanism which holds the blood pump and attaches to the patient.

23. A system as described in claim 22 wherein the holding mechanism includes a pump holding portion which holds the pump and a patient portion which is adapted to fit to the leg of the patient and to secure to the pump holding portion.

24. A system as described in claim 23 wherein the pump holding portion is made of plastic having an imprint of the shape of the blood pump in which the blood pump fits to be held by the pump holding portion, and the patient holding portion includes a band with loops and with straps having hooks adapted to wrap about the leg and the pump holding portion to hold the pump holding portion to the leg.

25. A system as described in claim 24 wherein the holding mechanism is adapted to attach to either leg of the patient and allow inflow or out flow to be connected to the contralateral side of the patient.

26. A system as described in claim 25 wherein the holding mechanism is adapted to hold the blood pump in a normal position or at an angle of 20 degrees from the normal position.

27. A system as described in claim 1 including means for delivering additional fluid into oxygenated blood by injecting a specific fluid into the blood pump mechanism.

28. A system as described in claim 27 wherein the delivering means includes an infusion system having an IV bag and the additional fluid is injected into the IV bag, and the fluid delivery depends upon the amount of fluid injected and the constant flow rate of the infusion system.

29. A system as described in claim 1 including a control system having a primary monitor and a backup monitor with a watchdog for monitoring the primary and backup monitors and independent redundant monitoring primary monitor and redundant backup monitor, the primary and backup, and redundant primary and redundant backup monitors each able to detect and manage single point faults of the system without requiring a dedicated 24 hours/day human surveillance.

30. A system as described in claim 1 wherein the pump mechanism has a pump inlet and provides circulatory support of blood flow over an entire physiologic pressure range without cavitation caused by excessive vacuum pressure at the pump inlet.

31. A system as described in claim 1 wherein the pump mechanism includes a motor and a controller having a motor control circuit that monitors motor drive output and initiates a logic signal when motor speed and direction as fed back from the motor does not agree with motor commands being output by the motor control circuit.

32. A system as described in claim 1 including a controller that can detect abnormal flow faults in a <50 ml/hour fluid flow pump mechanism based on the cyclic pressure profile of the pump mechanism.

33. A system as described in claim 1 wherein the transseptal cannula and the perfusion cannula are each interchangeable to quickly access or redistribute blood to a certain destination in a patient's body by changing appropriate sizes of the respective cannula.

34. A method for assisting blood flow by a patient's heart comprising the steps of:
  inserting percutaneously in the femoral vein of the patient and extending through the atrial septum from the right atrium to the left atrium a transseptal cannula;
  inserting percutaneously in the femoral artery a perfusion cannula for returning oxygenated blood to the arterial system of the patient;
  clamping a transseptal clamp mechanism to tubing within three feet of length connected to the transseptal cannula and a blood pump to avoid undesired disconnection of the blood pump and the transseptal cannula and undesired leaks at a connection joint formed between the blood pump and the transseptal cannula; and
  pumping blood with the blood pump through the tubing connected to the transseptal cannula and within three feet of length connected to the blood pump and the perfusion cannula at specified flow rates over a range of physiological pressures.

35. A method as described in claim 34 wherein the pumping step includes the step of pumping a continuous flow of blood with the blood pump.

36. A method as described in claim 35 wherein the pumping step includes the step of adjusting the flow of blood pumped with a controller connected to the blood pump.

37. A method as described in claim 36 wherein the adjusting step includes the step of adjusting impeller speed of an impeller of the blood pump to attain a desired flow of blood in the patient due to the operation of the blood pump.

38. A method as described in claim 37 including after the pumping step, there is the step of powering the controller and the blood pump with a battery as the patient is moved from a first location to a second location remote from the first location.

39. A method as described in claim 38 including before the pumping step, there are the steps of attaching a holding mechanism for the blood pump to the patient and placing the blood pump in the holding mechanism to hold the blood pump in place relative to the patient.

40. A method as described in claim 39 wherein the attaching step includes the step of attaching the holding mechanism to the leg of the patient.

41. A method as described in claim 40 wherein the placing step includes the step of wrapping straps of a band positioned about the leg of the patient, about the blood pump, and fixing hooks of the straps to loops of the band to secure the blood pump to the leg of the patient.

42. A method as described in claim 34 wherein the pumping step includes the step of pumping pulses of blood through the patient with a pulsatile pump.

43. A method as described in claim 42 wherein the pumping step includes the step of adjusting stroke timing of the pulsatile pump to obtain the desired pulse of blood flow through the patient.

44. A method as described in claim 34 including the step of implementing the inserting steps and the pumping step that can be implemented in a short time so as be practical for emergent use without open-chest surgery.

45. A system for assisting flow of blood by a patient's heart comprising:

a transseptal cannula adapted to be inserted percutaneously in a vein and extend through the atrial septum from the right atrium to the left atrium;

an extracorporeal blood pump mechanism having a blood pump for pumping blood received from the left atrium through the transseptal cannula that has been oxygenated, the blood pump inlet connected to the transseptal cannula;

a controller connected to the blood pump through which the operation of the blood pump speed is adjusted; and a perfusion cannula adapted to be inserted percutaneously in an artery for returning oxygenated blood to the arterial system of the patient, the perfusion cannula connected to the blood pump outlet, the extracorporeal blood pump is disposed within three feet of where the transseptal cannula and the output cannula are positioned to enter the patient.

* * * * *